United States Patent
Beard et al.

(10) Patent No.: US 6,452,032 B1
(45) Date of Patent: Sep. 17, 2002

(54) ORGANOSILYL COMPOUNDS HAVING NUCLEAR HORMONE RECEPTOR MODULATING ACTIVITY

(75) Inventors: Richard L. Beard; Michael E. Garst, both of Newport Beach; Roshantha A. Chandraratna, Laguna Hills, all of CA (US)

(73) Assignee: Allergan Sales, LLC, Irvine, CA (US)

( * ) Notice: Subject to any disclaimer, the term of this patent is extended or adjusted under 35 U.S.C. 154(b) by 42 days.

(21) Appl. No.: 09/591,042

(22) Filed: Jun. 9, 2000

Related U.S. Application Data

(60) Provisional application No. 60/138,731, filed on Jun. 11, 1999.

(51) Int. Cl.$^7$ .............................. C07F 7/10; C07F 7/08
(52) U.S. Cl. .................. 556/413; 556/419; 556/428; 556/438; 556/440; 556/422; 546/14; 548/110; 548/406; 549/214
(58) Field of Search .......................... 552/413, 419, 552/428, 438, 440, 422; 546/14; 548/110, 406; 549/214

(56) References Cited

U.S. PATENT DOCUMENTS

| | | |
|---|---|---|
| 5,053,523 A | 10/1991 | Chandraratna |
| 5,071,773 A | 12/1991 | Evans et al. |
| 5,278,318 A | 1/1994 | Chandraratna |
| 5,298,429 A | 3/1994 | Evans et al. |
| 5,324,744 A | 6/1994 | Chandraratna |
| 5,346,895 A | 9/1994 | Chandraratna |
| 5,348,972 A | 9/1994 | Chandraratna |
| 5,348,975 A | 9/1994 | Chandraratna |
| 5,407,937 A | 4/1995 | Chandraratna |
| 5,776,699 A | 7/1998 | Klein et al. |
| 5,877,207 A | 3/1999 | Klein et al. |

FOREIGN PATENT DOCUMENTS

WO  WO 00/40965  7/2000

OTHER PUBLICATIONS

Evans et al, "The Steroid and Thyroid Hormone Receptor Superfamily" Science vol. 240: 889–895 (May 1988).
Mangelsdorf et al, "The Retinoid Receptors", The Retinoids, Biology, Chemistry, and Medicine, Chapter 8, pp. 319–349, 1994.
Nagpal et al., "Retinoids as Anti–Cancer Agents", Current Pharm. Design 2:295–316 (1996).
Foreman et al, "Identification of a Nuclear Receptor That is Activated by Farnesol Metabolites", Cell vol. 81: 687–693 (1995).
Wang et al, "Endogenous Bile Acids Are Ligands for the Nuclear Receptor FXR/BAR", Molecular Cell vol. 3: 543–553 (May 1999).
Corey et al, "Useful Procedures for the Oxidation of Alcohols Involving Pyridinium Dichromate in Aprotic Media" Tet. Lett., No. 5, 399–402, 1979.
Omura et al., "Oxidation of Alcohols by "Activated" Dimethyl Sulfoxide. A Preparative, Steric and Mechanistic Study", Tetrahedron vol. 34, 1651–1660, (1978).
Komen et al, "Easy Preparation of 1,3–Di–Tert–Butylbenzene and Some Derivatives Thereof", Synthetic Communications, 26(9), 1693–1697 (1996).
Beadling et al, "Isolation of interleukin 2–induced immediate–early genes", Proc. Natl. Acad. Sci., vol. 90, pp. 2719–2723, Apr. 1993.
Boehm et al, "Synthesis and Structure–Activity Relationships of Novel Retinoid X Receptor–Selective Retinoids", J. Med. Chem. 1994, 37, 2930–2941.

*Primary Examiner*—Paul F. Shaver
(74) *Attorney, Agent, or Firm*—Carlos A. Fisher; Robert J. Baran; Martin A. Voet

(57) ABSTRACT

Silicone-containing organic compounds useful as modulators of mammalian nuclear hormone receptors, particularly the retinoid receptors and the farnesoid receptors.

34 Claims, No Drawings

ORGANOSILYL COMPOUNDS HAVING NUCLEAR HORMONE RECEPTOR MODULATING ACTIVITY

This application claims priority under 35 USC 119(e) to Provisional Patent Application Serial No. 60/138,731, filed Jun. 11, 1999, hereby incorporated by reference herein.

FIELD OF THE INVENTION

The present invention is relevant to the fields of human and veterinary medicine, physiology and biochemistry, particularly in the regulation of cellular proliferation and lipid metabolism in a mammal.

BACKGROUND OF THE INVENTION

A vast array of specific metabolic, developmental, and catabolic processes appear to be directly or indirectly regulated in vivo by comparatively small molecules such as steroids, retinoids and thyroid hormones. The mechanism whereby a single such compound can contribute to the regulation of numerous different cellular events was the subject of much speculation until relatively recently, when it was discovered that these compounds each share the ability to bind to transcriptionally active proteinaceous receptors. These protein receptors, in turn, are able to bind specific cis-acting nucleic acid regulatory sequence regions, termed response elements or RE's, located upstream of the coding sequence of certain genes and to activate the transcription of these genes. Thus, the proteinaceous receptors can serve as specific, ligand-dependent regulators of gene transcription and expression.

The amino acid sequences of these various receptors were quickly found to share regions of homology, thus making each such receptor a member of a family of ligand-modulated receptor molecules. This family has been termed the steroid superfamily of nuclear hormone receptors; nuclear, because the receptors are usually found in high concentration in the nucleus of the cell.

Further study of the structural and functional relationship between the nuclear hormone receptors has shown certain characteristics in common between them in addition to sequence homology. See e.g., Evans et al. *Science* 240:889–895 (1988). As stated above, the nuclear hormone receptors are able to bind to cis-acting regulatory elements present in the promoters of the target genes. The glucocorticoid, estrogen, androgen, progestin, and mineralcorticoid receptors have been found to bind as homodimers to specific response elements organized as inverted repeats.

Another class of nuclear hormone receptors, which includes the retinoid receptor RAR (retinoic acid receptor), the thyroid receptor, the vitamin D receptor, the peroxysome proliferator receptor, and the insect ecdysone receptor bind the response element as a heterodimer in conjunction with the retinoid X receptor (RXR), which is positively activated by 9-cis retinoic acid. See Mangelsdorf, et al., *The Retinoid Receptors in The Retinoids: Biology, Chemistry and Medicine* Ch.8 (Sporn et al., eds. 2d ed., Raven Press Ltd. 1994); Nagpal and Chandraratna, *Current Pharm. Design* 2:295–316 (1996), which are both incorporated by reference herein. The retinoid receptors RAR and RXR, like many nuclear hormone receptors, exist in a number of subtypes (RARα, RARβ, RARγ, and RXRα, RXRβ, and RXRγ). Additionally, each subtype may exist in different isoforms.

Another such receptor is a relatively recently characterized nuclear hormone receptor termed farnesoid X-activated receptor (FXR). Foreman et al., *Cell* 81:687–693 (1995) have demonstrated that this receptor termed farnesoid X-activated receptor (FXR), is activated by farnesol and related molecules. This reference is hereby incorporated by reference herein. FXR expression is largely restricted to the liver, gut, adrenal gland, and kidney.

Common to other nuclear hormone receptors, the amino acid sequence of FXR reveals a conserved DNA-binding domain (DBD) and ligand-binding domain (LBD). The LBD comprises subdomains responsible for ligand binding, receptor dimerization, and transactivation. Additionally, cells expressing chimeric proteins that contain the LBD of FXR fused to the DBD of the yeast GAL4 transcription activator did not transcribe a reporter gene containing a GAL4 response element unless the FXR construct was coexpressed with another protein comprising the dimerization and ligand binding subdomains of RXR. These data suggested that FXR and RXR interact to form a transcriptionally active dimer. No interaction was seen between FXR and any other nuclear hormone receptor. Id.

FXR has been recently discovered to be an important regulator of bile acid synthesis. When bound by an appropriate ligand FXR is activated, and functions to regulate the expression of Cyp7a, thereby controlling a key stage in the degradation of cholesterol, the precursor of the bile acids and the steriod hormones. See Wang, et al., *Molec. Cell* 3:543–553 (May 1999), hereby incorporated by reference herein.

SUMMARY OF THE INVENTION

The present invention is directed to silicone-containing organic compounds is and compositions comprising such compounds having the general structure indicated in Formulae 1–4, infra. Such compounds are useful to modulate the transcription-regulating activity of a nuclear hormone receptor, such as, without limitation, a retinoic acid receptor (RAR), a retinoid X receptor (RXR), a farnesoid receptor (FXR), perioxisome proliferator activated receptor (PPAR) and the like. Certain such compounds are ligands of either or both an RAR or an RXR, and able to cause the retinoid receptor to suppress, inhibit, or stimulate the transcription of a given target gene. Preferably, in this embodiment of the present invention the claimed compounds are substantially specific in their activity towards either RXR or RAR, and do not activate or inhibit any other nuclear hormone receptor.

Certain compounds of the present invention may have activity at one or more nuclear hormone receptor other than a retinoid receptor, such as, without limitation, FXR, PPAR, TR, DAX, CAR. Preferably, the compound is active as a modulator of FXR activity. It is also preferred, although not essential, that the compound is not substantially active as a modulating ligand of other nuclear hormone receptors.

It has also been discovered that the compounds of the present invention have activity as agonists, antagonists, or inverse agonists of the transactivation activity of nuclear hormone receptors. Certain compounds of the present invention have RAR and/or RXR agonist activity in a transactivation assay using a reporter gene as a transcription template.

Certain compositions of the invention comprise a compound active as an FXR agonist or antagonist that is able to modulate concentrations of plasma cholesterol in a mammal. In another embodiment the FXR agonist may be used to increase the concentration of cholesterol within a hypocholesteremic mammal. As stated above, FXR has been discovered to inhibit Cyp7a expression when bound and activated by bile acids. Thus, an antagonist of FXR would prevent the bile acid-initiated inhibition of Cyp7a synthesis.

The nuclear hormone receptor ligands of the present invention may be receptor agonists, receptor antagonists, or receptor inverse agonists. By "agonist" is meant that the ligand stimulates a ligand-dependent receptor-characteristic activity above any baseline levels present in the absence of ligand. By "receptor-characteristic activity" is meant the direct or indirect inhibition or stimulation of gene expression, which expression is regulated by the receptor in question. By "antagonist" is meant that the ligand binds to the receptor and functions as a competitive or non-competitive inhibitor of receptor-characteristic agonist activity. By "inverse agonist" or "reverse agonist" is meant that the ligand will bind to the receptor in question and cause the suppression of receptor activity lower than the amount of activity seen in the absence of receptor ligand.

Thus, the present invention pertains to compositions comprising, consisting essentially of, or consisting of a compound selected from the group consisting of Formulas 1, 2, 3 and 4

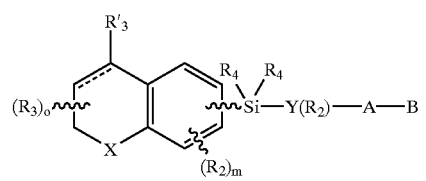

Formula 1

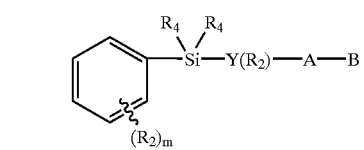

Formula 2

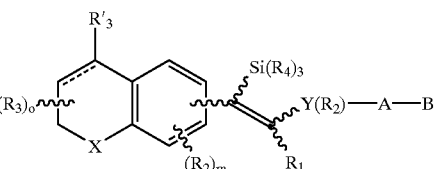

Formula 3

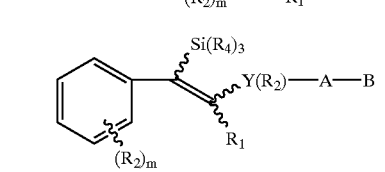

Formula 4 wherein the dashed line represents a bond or absence of a bond;

X is S, O, NR' where R' is H or alkyl of 1 to 6 carbons, or

X is $(C(R_1)_2)_n$ where $R_1$ is H or alkyl of 1 to 6 carbons, and n is an integer having the value of 0 or 1;

$R_2$ is hydrogen, lower alkyl of 1 to 6 carbons, F, Cl, Br, I, $CF_3$, fluoro substituted alkyl of 1 to 6 carbons, OH, SH, alkoxy of 1 to 12 carbons, or alkylthio of 1 to 12 carbons, benzyloxy or $C_1$–$C_{12}$ alkylbenzyloxy;

$R_3$ is hydrogen, lower alkyl of 1 to 6 carbons or F; m is an integer having the value of 0–3;

o is an integer having the value of 0–4 when the dashed line represents absence of a bond, and 0–3 when the dashed line represents a bond;

$R_3'$ is hydrogen, lower alkyl of 1 to 6 carbons, F or $R_3'$ is hydrogen, lower alkyl of 1 to 6 carbons, F or $(R_{15})_r$-phenyl, $(R_{15})_r$-naphthyl, or $(R_{15})_r$-heteroaryl where the heteroaryl group has 1 to 3 heteroatoms selected from the group consisting of O, S and N, r is an integer having the values of 0–5;

$R_4$ is alkyl of 1 to 8 carbons, or phenyl;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

$R_{15}$ is independently H, F, Cl, Br, I, $NO_2$, $N(R_8)_2$, $NH(R_8)$, $COR_8$, $NR_8CON(R_8)_2$, OH, $OCOR_8$, $OR_8$, CN, an alkyl group having 1 to 10 carbons, fluoro substituted alkyl group having 1 to 10 carbons, an alkenyl group having 1 to 10 carbons and 1 to 3 double bonds, alkynyl group having 1 to 10 carbons and 1 to 3 triple bonds, or a trialkylsilyl or trialkylsilyloxy group where the alkyl groups independently have 1 to 6 carbons;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH, $NO_2$, $P(O)(OH)_2$, $P(O)(OH)OR_8$, $P(O)(OR_8)_2$, $SO_2OH$, $SO_2(OR_8)$, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, or a pharmaceutically acceptable salt of said compound.

Other aspects and embodiments of the invention are contained in the disclosure that follows and the claims that conclude this specification.

DETAILED DESCRIPTION OF THE INVENTION

The present invention is directed to compositions capable of modulating the activity of a mammalian nuclear hormone receptor, preferably the human RXR, RAR or FXR receptor proteins.

Such compositions comprise compounds that will bind a nuclear hormone receptor, thereby affecting the biological activity of the receptor, either directly or by blocking the ability of a naturally occurring receptor ligand to exert its effects on the receptor. In certain embodiments, the compositions of the present invention will also contain a pharmaceutically acceptable excipient or carrier. The compositions of the present invention may comprise antagonists, agonists, or inverse agonists of the receptor. Preferably, although not necessarily, the compounds have activity at a single receptor type and have no substantial activity at other nuclear hormone receptors.

Also included within the scope of the invention are aspects directed to compositions comprising a pharmaceutically acceptable composition comprising a receptor agonist, antagonist or inverse agonist for treatment of a medical condition. In one aspect, the receptor is an RAR agonist, and the medical condition is a disease or condition, such as acne, psoriasis, rheumatoid arthritis and viral infections. RAR active compounds are well known to be useful for the treatment of such conditions.

In another aspect the composition comprises a pharmaceutically acceptable composition comprising an FXR antagonist, as disclosed herein. Such a compound, effectively blocking the inhibition of bile acid synthesis by bile acids, would promote the synthesis of bile acids though the breakdown of cholesterol.

Specifically, the compounds of the present invention are silicone-containing organic compounds of the general structure indicated below.

The compounds of this invention are useful as regulators of cell proliferation and differentiation and of lipid metabolism, and particularly as agents for treating dermatoses, such as acne, Darier's disease, psoriasis, icthyosis, eczema and atopic dermatitis, and for treating and preventing malignant hyperproliferative diseases such as epithelial cancer, breast cancer, prostatic cancer, head and neck cancer and myeloid leukemias, for reversing and preventing atherosclerosis and restenosis resulting from neointimal hyperproliferation, for treating and preventing other non-malignant hyperproliferative diseases such as endometrial hyperplasia, benign prostatic hypertrophy, proliferative vitreal retinopaythy and dysplasias, for treating autoimmune diseases and immunological disorders (e.g. lupus erythematosus), for treating chronic inflammatory diseases such as pulmonary fibrosis, for treating and preventing diseases associated with lipid metabolism and transport such as dyslipidemias, hypercholesterolemia and hypocholesterolemia, for promoting wound healing, for treating dry eye syndrome and for reversing and preventing the effects of sun damage to skin.

In the treatment of dermatoses, it will generally be preferred to administer the drug topically, though in certain cases such as treatment of severe cystic acne, oral administration may also be used. Any common topical formulation such as a solution, suspension, gel, ointment, or salve and the like may be used. Preparation of such topical formulations are well described in the art of pharmaceutical formulations as exemplified, for example, Remnington's Pharmaceutical Science, Edition 17, Mack Publishing Company, Easton, Pa. For topical application, these compounds could also be administered as a powder or spray, particularly in aerosol form.

If the drug is to be administered systemically, it may be confected as a powder, pill, tablet or the like, or as a syrup or elixir for oral administration. For intravenous or intraperitoneal administration, the compound will be prepared as a solution or suspension capable of being administered by injection. In certain cases, it may be useful to formulate these compounds in suppository form or as an extended release formulation for deposit under the skin, as a transdermal delivery system, or by intermuscular injection.

Other medicaments can be added to such topical formulation for such secondary purposes as treating skin dryness, providing protection against light; other medications for treating dermatoses, preventing infection, reducing irritation, inflammation and the like.

Treatment of dermatoses or any other indications known or discovered to be susceptible to treatment by retinoic acid or farnesoid receptor modulators will be effected by administration of the therapeutically effective dose of one or more compounds of the instant invention. A therapeutic concentration will be that concentration which effects a reversal or inhibition of the particular condition, or retards its expansion. In certain instances, the drug potentially could be used in a prophylactic manner to prevent onset of a particular condition. A given therapeutic concentration will vary from condition to condition and in certain instances may vary with the severity of the condition being treated and the patient's susceptibility to treatment. Accordingly, a given therapeutic concentration will be best determined at the time and place through routine experimentation. However, it is anticipated that in the treatment of, for example, acne, or other such dermatoses, that a formulation containing between 0.001 and 5 percent by weight, preferably about 0.01 to 1% will usually constitute a therapeutically effective concentration. If administered systemically, an amount between 0.01 and 100 mg per kg body weight per day, but preferably about 0.1 to 10 mg/kg, will effect a therapeutic result in most instances.

EXAMPLE 1

Retinoic acid receptor transactivation activity and binding efficiencies were determined essentially as described in U.S. Pat. Nos.: 5,298,429 and 5,071,773, incorporated by reference herein. Transactivation assays employed expression plasmids encoding the full length receptors RARα, RARβ, RARγ, RXRα, RXRβ, and RXRγ. Reporter plasmids contained the herpes virus thymidine kinase promoter and the appropriate retinoid acid receptor response element (RAREs) or retinoid X receptor response element (RXREs) positioned upstream of an open coding region encoding firefly luciferase.

Binding assays were performed using a classic competition assay format in which cloned receptor RAR mand RXR molecules were first loaded with either radiolabeled all-trans-retinoic acid (RAR) or radiolabeled 9-cis retinoic acid (RXR), and then the amount of radioactivity liberated with increasing concentration of test compound was measured.

The tested exemplary compounds had the following structures:

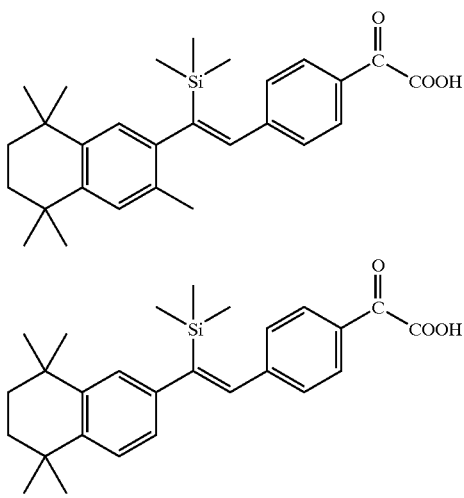

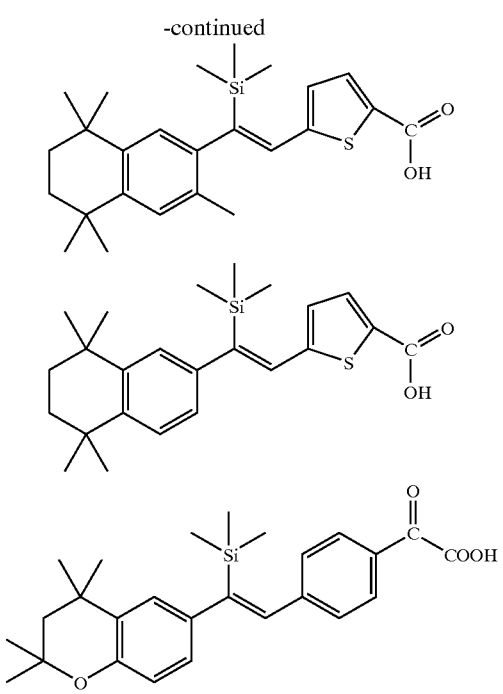

These compounds are designated AGN 192192, AGN 192337, AGN 192294, AGN 192295, and AGN 192452, respectively. $EC_{50}$ designates the concentration of the tested compound which was able to give a 50% maximal transcription of the reporter gene; $KD_{50}$ indicates the concentration of the tested compound at which 50% of the compound molecules are bound to the receptor. NT indicates those points that were not tested in the particular experiment. Results were as follows.

| AGN Number | Assay | RARα | RARβ | RARγ | RXRα | RXRβ | RXRγ |
|---|---|---|---|---|---|---|---|
| 192192 | Trans ($EC_{50}$) | 550 | 88 | NA | 990 | 780 | 960 |
|  | Bind ($KD_{50}$) | 2640 | 699 | 2022 | $>10^3$ | $>10^3$ | $>10^3$ |
| 192337 | Trans ($EC_{50}$) | NA | 260 | 1500 | NA | NA | NA |
|  | Bind ($KD_{50}$) | 2279 | 2426 | 5836 | NT | NT | NT |
| 192294 | Trans ($EC_{50}$) | NA | NA | NA | 0 | 0 | 0 |
|  | Bind ($KD_{50}$) | 0 | 7998 | 8937 | NT | NT | NT |
| 192295 | Trans ($EC_{50}$) | 350 | 290 | 330 | 0 | 0 | 0 |
|  | Bind ($KD_{50}$) | 1296 | 499 | 1551 | NT | NT | NT |
| 192452 | Trans ($EC_{50}$) | 0 | 0 | 0 | 3100 | 0 | 2900 |
|  | Bind ($KD_{50}$) | 0 | 3299 | 4523 | NT | NT | NT |

The results indicate that the tested compounds are able to simulate the receptor-mediated activation of reporter gene expression in these experiments.

The following example provides a detailed description of how to make the compounds of the invention. Those of skill in the art will recognize that the structures of the receptor agonists (such as those tested in Example 1 above) may be used to select one or more common feature for the molecular modeling of other FXR agonists. Similarly, much is known about the type of modifications that may be made to a receptor agonist to convert it into an antagonist, given the structure of a receptor agonist like those presented above. Indeed, modifications to a receptor agonist have already been made in the design of antagonists and inverse agonists of the retinoid receptors. See e.g., U.S. Pat. No. 5,776,699, incorporated by reference herein. Since an agonist binds to the LBD of the nuclear hormone to exert its effect, the modification of such an agonist to create a receptor antagonist generally involves retention of the same general structure as the agonist (thus permitting the antagonist to continue to bind the receptor) combined with the addition of somewhat "bulky" groups to prevent the specific interaction between receptor and the bound compound that results in activation of the activity of the receptor.

Thus, in the present case, an antagonist or inverse agonist would be expected by the person or ordinary skill in the art to have a structure similar to that of the agonists listed above. For example, an antagonist would contain one or more modifications selected from, without limitation and with reference to AGN 192337, addition of an aryl group to the cyclohexyl moiety, particularly at the uppermost position of the ring (relative to Formulae 1–4, infra); addition of an alkyl group greater than two carbons in length, or an aryl group at the silyl moiety, and addition of an aryl group to the carbon at the unsubstituted double bond to the right of the trimethylsilyl substitution. Other such modifications will be apparent to the person of skill in the art, and are contained in Example 2 and the claims that conclude this specification.

EXAMPLE 2

General Embodiments and Synthetic Methodology

Definitions

The term alkyl refers to and covers any and all groups which are known as normal alkyl, branched-chain alkyl and cycloalkyl. The term alkenyl refers to and covers normal alkenyl, branch chain alkenyl and cycloalkenyl groups having one or more sites of unsaturation. Similarly, the term alkynyl refers to and covers normal alkynyl, and branch chain alkynyl groups having one or more triple bonds.

Unless specified otherwise, lower alkyl means the above-defined broad definition of alkyl groups having 1 to 6 carbons in case of normal lower alkyl, and as applicable 3 to 6 carbons for lower branch chained and cycloalkyl groups. Lower alkenyl is defined similarly having 2 to 6 carbons for normal lower alkenyl groups, and 3 to 6 carbons for branch chained and cyclo- lower alkenyl groups. Lower alkynyl is also defined similarly, having 2 to 6 carbons for normal lower alkynyl groups, and 4 to 6 carbons for branch chained lower alkynyl groups.

The term "ester" as used here refers to and covers any compound falling within the definition of that term as classically used in organic chemistry. It includes organic and inorganic esters. Where B of Formula 1, 2, 3 or 4 is —COOH, this term covers the products derived from treatment of this function with alcohols or thiols preferably with aliphatic alcohols having 1–6 carbons. Where the ester is derived from compounds where B is —$CH_2OH$, this term covers compounds derived from organic acids capable of forming esters including phosphorous based and sulfur based acids, or compounds of the formula —$CH_2OCOR_{11}$ where $R_{11}$ is any substituted or unsubstituted aliphatic, aromatic, heteroaromatic or aliphatic aromatic group, preferably with 1–6 carbons in the aliphatic portions.

By "synthetic compound" is meant an organic compound that does normally not occur in a mammal. Specifically, a synthetic compound is meant to exclude a naturally occurring bile acid.

Unless stated otherwise in this application, preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Also preferred are the phenyl or lower alkyl phenyl esters.

Amide has the meaning classically accorded that term in organic chemistry. In this instance it includes the unsubstituted amides and all aliphatic and aromatic mono- and di-substituted aramides. Unless stated otherwise in this application, preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from substituted and unsubstituted lower alkyl amines. Also preferred are mono- and disubstituted amides derived from the substituted and unsubstituted phenyl or lower alkylphenyl amines. Unsubstituted amides are also preferred.

Acetals and ketals include the radicals of the formula-CK where K is (—OR)$_2$. Here, R is lower alkyl. Also, K may be —$OR_7O$— where $R_7$ is lower alkyl of 2–5 carbon atoms, straight chain or branched.

A pharmaceutically acceptable salt may be prepared for any compound in this invention having a functionality capable of forming a salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

Many compounds of the present invention have trans and cis (E and Z) isomers. Specific orientation of substituents relative to a double bond is indicated in the name of the respective compound, and/or by specifically showing in the structural formula the orientation of the substituents relative to the double bond. Unless it is specifically stated otherwise the invention covers trans as well as cis isomers. Where the chemical name indicates a specific isomer, that designation by name is intended to control over a structure that may be ambiguously drawn or shows a different isomer.

Some of the compounds of the present invention may contain one or more chiral centers and therefore may exist in enantiomeric and diastereomeric forms. The scope of the present invention is intended to cover all isomers per se, as well as mixtures of cis and trans isomers, mixtures of diastereomers and racemic mixtures of enantiomers (optical isomers) as well.

With reference to the symbol Y in Formulas 1, 2, 3 and 4 the preferred compounds of the invention are those where Y is phenyl, naphthyl, pyridyl, thienyl or furyl. Even more preferred are compounds where Y is phenyl. As far as substititutions on the Y (phenyl) and Y (pyridyl) groups are concerned, compounds are preferred where the phenyl group is 1,4 (para) substituted and where the pyridine ring is 2,5 substituted. (Substitution in the 2-position in the "pyridine" nomenclature corresponds to substitution in the 6-position in the "nicotinic acid" nomenclature.) In the presently preferred compounds of the invention there is no $R_2$ substituent on the Y group.

The A-B group of the preferred compounds is $(CH_2)_q$ COOH or $(CH_2)_q$—COOR$_8$, where $R_8$ is defined as above. Even more preferably q is zero and $R_8$ is lower alkyl or (trialkylsilyl)ethyl (or alkyl) or (trimethylsilyl)ethyl and more prefereably $R_8$ is hydrogen. Compounds are also preferred where the A-B group is $CH_2OH$.

With reference to the group X in Formulas 1 and 3, in the presently preferred compounds of the invention X is O (chroman or chromene compounds) or X represents $C(R_1)_2$ (tetrahydronaphthalene or dihydronaphthalene derivatives). Even more preferably $R_1$ of $C(R_1)_2$ is methyl.

$R_2$ is preferably hydrogen or lower alkyl, even more preferably methyl and $R_2$ is preferably in the 3 position of the tetrahydronaphthalene and dihydronaphthalene moiety, and preferably in the 8 position of the chroman, chromen, thiochroman, thiochromen, dihydro or tetrahydroquinoline moiety. When $R_2$ is other than hydrogen then preferably there is only one $R_2$ substituent in the aromatic portion of the condensed ring.

$R_3$ is preferably hydrogen or methyl. Presently most preferred substitution of the non-aromatic portion of the condensed ring when the dashed line represents absence of a bond in Formulas 1 and 3 is such that there are germinal dimethyl groups in the 6 or 8 positions, or in both when X is a heteroatom, and germinal dimethyl groups in the 5 and 8 positions when the condensed ring is tetrahydronaphthylene and germinal dimethyl groups in the 5-position when the condensed ring is dihydronaphthalene. When the dashed line represents a bond, $R_3$ is preferably $(R_{15})_r$-phenyl, $(R_{15})_r$-naphthyl, or $(R_{15})_r$-heteroaryl, more preferably $(R_{15})_r$-phenyl, or $(R_{15})_r$-thienyl and $R_{15}$ preferably is an alkyl group. As represented herein, numbering of the bicyclic ring structure is as follows.

In the presently preferred compounds of the invention the silicon containing substituent is preferably attached at the 6 position of the chroman, chromene, thiochroman, thiochromene, tetrahydroquinoline or dihydroquinoline nucleus, and to the 2 position of the tetrahydronaphthalene or dihydronaphthalene nucleus.

The present specific examples of the compounds of the invention are disclosed in TABLE 1 with reference to Formula 5 and Formula 6 and their preparation by the presently preferred synthetic methodology is described in the alcohol function. An example of a suitable reagent to introduce the protecting group and one that is used in the synthesis of the presently preferred compounds of the invention is tert-butyldiphenylsilyl chloride shown in Reaction Scheme 1. The product of the reaction with tert-butyldiphenylsilyl chloride (conducted in the presence of base) is a (bromoaryl)methyl t-butyldiphenylsilyl ether of Formula 8.

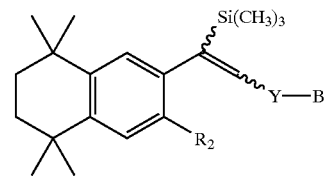

Formula 5

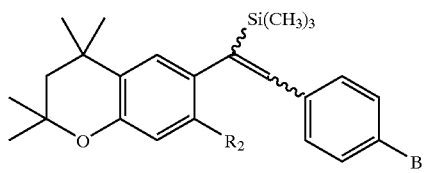

Formula 6

TABLE 1

| Compound | Formula | $R_2$ | Y | B |
|---|---|---|---|---|
| 3 | 5 | $CH_3$ | 1,4 substituted phenyl | $CH_2OH$ |
| 4 | 5 | $CH_3$ | 1,4 substituted phenyl | COOEt |
| 5 | 5 | $CH_3$ | 1,4 substituted phenyl | COOH |
| 6 | 5 | H | 1,4 substituted phenyl | $CH_2OH$ |
| 7 | 5 | H | 1,4 substituted phenyl | COOEt |
| 8 | 5 | H | 1,4 substituted phenyl | COOH |
| 10 | 6 | H | — | COOEt |
| 11 | 6 | H | — | COOH |
| 14 | 5 | $CH_3$ | 2,5 substituted thienyl | $CH_2OH$ |
| 15 | 5 | $CH_3$ | 2,5 substituted thienyl | COOEt |
| 16 | 5 | $CH_3$ | 2,5 substituted thienyl | COOH |
| 17 | 5 | H | 2,5 substituted thienyl | $CH_2OH$ |
| 18 | 5 | H | 2,5 substituted thienyl | COOEt |
| 19 | 5 | H | 2,5 substituted thienyl | COOH |

The compounds of the invention can be made by the generalized synthetic route shown in Reaction Scheme 1, 1a and Reaction Scheme 2.

Referring now to Reaction Scheme 1 and Reaction Scheme 1a, a presently preferred synthetic route to compounds of the invention of Formula 3 is disclosed. In accordance with Scheme 1 a bromoarylmethyl alcohol compound of Formula 7 is the starting material. In Formula 7 the symbols Y and $R_2$ are defined as in connection with Formulas 1–4. Examples for the compounds of Formula 7 which are used for the synthesis of presently preferred exemplary compounds of the invention are 4-bromobenzyl alcohol and (5-bromothiophen-2-yl)-methyl alcohol. Other examples are 3-bromobenzyl alcohol, (6-bromopyridin-3-yl)methyl alcohol and (5-bromofuran-2-yl)methyl alcohol. These starting materials are either available commercially or can be readily obtained in accordance with the chemical literature. The alcohols of Formula 7 are reacted with a reagent that introduces a protecting group on the primary

REACTION SCHEME 1

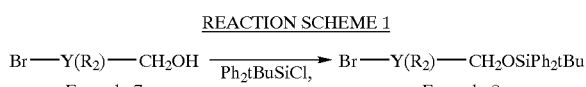

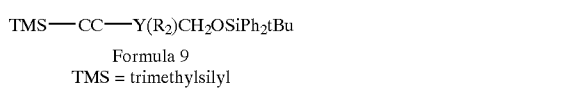

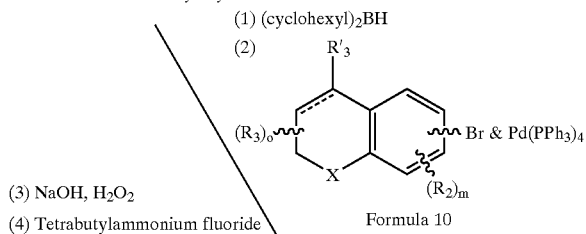

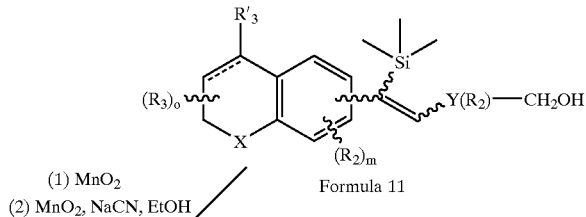

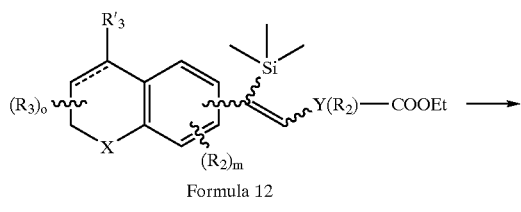

HOMOLOGS AND DERIVATIVES

REACTION SCHEME 1a

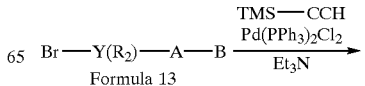

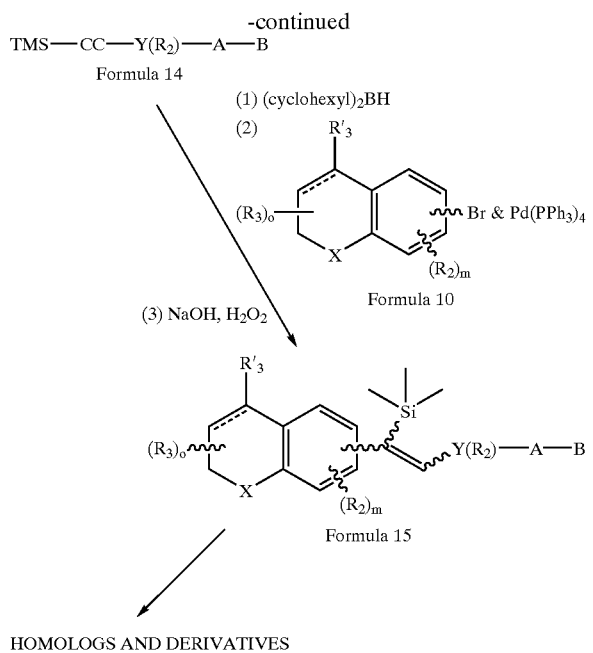

HOMOLOGS AND DERIVATIVES

The (bromoaryl)methyl t-butyldiphenylsilyl ether of Formula 8 is reacted with (trimethylsilyl)acetylene in the presence of bis(triphenylphosphine)palladium (II) chloride catalyst, copper (I) iodide and a suitable base such as triethylamine. The latter coupling reaction of a bromoaryl compound with (trimethylsilyl)acetylene in the presence of a palladium complex catalyst per se is well known in the art, and is described for example in U.S. Pat. Nos. 5,663,347 and 5,808,083 the specification of which are expressly incorporated herein by reference. The product of the coupling reaction with (trimethylsilyl)acetylene is a ((trimethylsilyl)ethynylaryl)methyl t-butyldiphenylsilyl ether of Formula 9.

Referring now to Reaction Scheme 1a, the starting material is a bromoaryl compound of Formula 13 where the symbols Y, $R_2$, A, and B are again defined as in connection with Formulas 1–4. Examples for the starting compounds of Formula 13 are ethyl 4-bromobenzoate, ethyl 6-bromonicotinate, ethyl 2-bromothiophene-3-carboxylate and ethyl 2-bromofuran-3-carboxylate. These and analogous bromoaryl esters are readily available in accordance with the chemical literature. The bromoaryl compound of Formula 13 is reacted with (trimethylsilyl)acetylene in the same manner as described in Reaction Scheme 1, to provide the (trimethylsilyl)ethynylaryl compounds of Formula 14. It will be, of course, readily apparent to those skilled in the art that instead of the bromo derivatives the appropriate iodo derivatives can also be used in the the compounds of Formula 7 and Formula 13.

In the next step of the reaction sequence shown both in Reaction Scheme 1 and 1a, the (trimethylsilyl)ethynylaryl compounds of Formula 9 (Scheme 1) or of Formula 14 (Scheme 1a) is reacted with bis(cyclohexanyl)borane, which is prepared by reacting borane methyl sulfide with two equivalents of cyclohexene in an ethereal solvent such as tetrahydrofuran (THF). Bis(cyclohexanyl) borane, which is indicated in the reaction scheme, reacts with the (trimethylsilyl)ethynylaryl compounds of Formula 9 (Scheme 1) or of Formula 14 (Scheme 1a) to form an intermediate adduct. This adduct is reacted in the presence of tetrakis(triphenylphosphine)palladium (0) in an ethereal solvent, such as TBF, with a bromoaryl compound of Formula 10. The coupling of the bromo (or iodo) aryl compound of Formula 10 with the adduct is typically conducted under reflux conditions in an inert (argon) gas atmosphere. Base (NaOH) and hydrogen peroxide is then added to the reaction mixture to provide the (trimethylsilyl) vinyl product of Formula 15 in Scheme 1a. In accordance with Scheme 1 product of the coupling reaction still includes the diphenyl-t-butylsilyl protecting group which is removed by treatment with tetrabutylammonium fluoride to give the (trimethylsilyl)vinyl) aryl methyl alcohol derivatives of Formula 11.

The condensed cyclic bromoaryl compounds of Formula 10 which are used in the coupling reaction are available in accordance with the chemical scientific or patent literature, or can be obtained within the skill of the ordinary artisan in analogy to synthetic processes known in the scientific or patent literature. Examples for compounds of Formula 10 which are used for the preparation of presently preferred compounds of the invention are 2-bromo-3,5,5,8,8-pentamethyl-5,6,7,8-tetrahydronaphthalene, 2-bromo-5,5,8,8-tetramethyl-5,6,7,8-tetrahydronaphthalene and 6-bromo-2,2,4,4-tetramethylchroman. Further examples are 6- or 7-bromo-4,4-dimethylchroman, 6- or 7-bromo-4,4-dimethylthiochroman and 2 or 3 bromo tetrahydroquinoline derivatives which are available in accordance with the teachings of U.S. Pat. Nos. 5,348,972, 5,053,523 and 5,877,207 the specifications of which are incorporated herein by reference. As still further examples U.S. Pat. Nos. 5,278,318, 5,407,937, and 5,407,937 describe 2-alkyl and/or 4-alkyl substituted thiochromans also substituted with a bromo group in the 6 position. U.S. Pat. No. 5,346,585 describes 2-alkyl and/or 4-alkyl substituted thiochromans substituted with a bromo group in the 7 position. U.S. Pat. Nos. 5,324,744, 5,348,975 and 5,346,585 describe 2-alkyl and/or 4-alkyl substituted chromans substituted with a bromo group in the 7 position. U.S. Pat. No. 5,348,972 describes 4-alkyl substituted tetrahydroquinoline compounds substituted with a bromo group in the 2-position. The specifications of U.S. Pat. Nos. 5,278,318, 5,324,744, 5,346,585, 5,348,975, and 5,407,937 are also expressly incorporated herein by reference.

Condensed cyclic bromoaryl compounds of Formula 10 where the dashed line represents a bond, and particularly those where the dashed line represents a bond and the $R'_3$ substituent is an aryl or heteroaryl group, can be obtained from the corresponding brorninated chroman-4-one, thiochroman-4-one, tetrahydroquinoline-4-one, and tetrahydronaphthalenone derivatives by first forming the (trifluoromethyl)sulfonyloxy derivatives from the oxo functionality, and thereafter reacting those with an (organometallic) derivative that introduces the $R'_3$ group in analogy to the reactions described in U.S. Pat. No. 5,877,207. Alternatively, the compounds of the invention where the dashed line represents a bond and the $R^1_3$ substituent is an aryl or heteroaryl group, can be obtained from the corresponding (trimethylsilyl)vinyl derivatives that include an oxo function in the 4-position of the chroman, thiochroman or tetrahydroquinoline, and in the 8-position of tetrahydronaphthalene nucleus. These reactions are also conducted through the (trifluoromethyl)sulfonyloxy intermediates, in analogy to the teachings of U.S. Pat. No. 5,877,207.

Referring now again to Reaction Scheme 1, the primary alcohol derivatives of Formula 11 are compounds within the scope of the invention, particularly within the scope of Formula 3. The primary alcohols can be oxidized to the ester stage, for example as shown in Scheme 1, by treatment with manganese dioxide that first oxidizes the primary alcohol to the aldehyde stage, and thereafter by treatment of the aldehyde with manganese dioxide and sodium cyanide in alcohol, to provide the ethyl ester derivatives of Formula 12. The compounds of Formula 11, and 12 in Reaction Scheme 1, and the compounds of Formula 15 in Reaction Scheme 1a can be converted to further compounds of the invention by synthetic procedures which are well known in the art. This is indicated in Reaction Schemes 1 and 1a as conversion to "Homologs and Derivatives" and the transformations symbolized here primarily refer to reactions of the group designated A-B in the formulas. In these and related reactions the following well known and published general principles and synthetic methodology can be employed.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide (DCC) and 4-(dimethylamino)pyridine (DMAP). The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups*, Ed. Greene, John Wiley & Sons, 1981.

The acids and salts derived from compounds of the invention are readily obtainable from the corresponding esters. Basic saponification with an alkali metal base will provide the acid. For example, an ester of the invention may be dissolved in a polar solvent such as an alkanol, preferably under an inert atmosphere at room temperature, with about a three molar excess of base, for example, lithium hydroxide or potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the ester is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 1–4 hours, preferably 2 hours. Solvent removal provides a residue which is taken up in an inert organic solvent such as benzene, cooled to about 0 degrees C. and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alkyl halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/oxalyl chloride in methylene chloride (Omura, K., Swern, D., *Tetrahedron*, 1978. 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

The compounds of the invention which are in accordance with Formula 4 can be prepared in analogy to the synthetic routes described in Reaction Schemes 1 and 1a. In order to obtain these compounds of the invention, a halogenated benzene derivative, such as bromobenzene, iodobenzene (or a substituted derivative thereof where the substituent is $R_2$) is reacted with the (trimethylsilyl)ethynylaryl compounds of Formula 9 (Scheme 1) or of Formula 14 (Scheme 1a).

Referring now to Reaction Scheme 2, a synthetic route is described to obtain compounds of the invention in accordance with Formula 1.

REACTION SCHEME 2

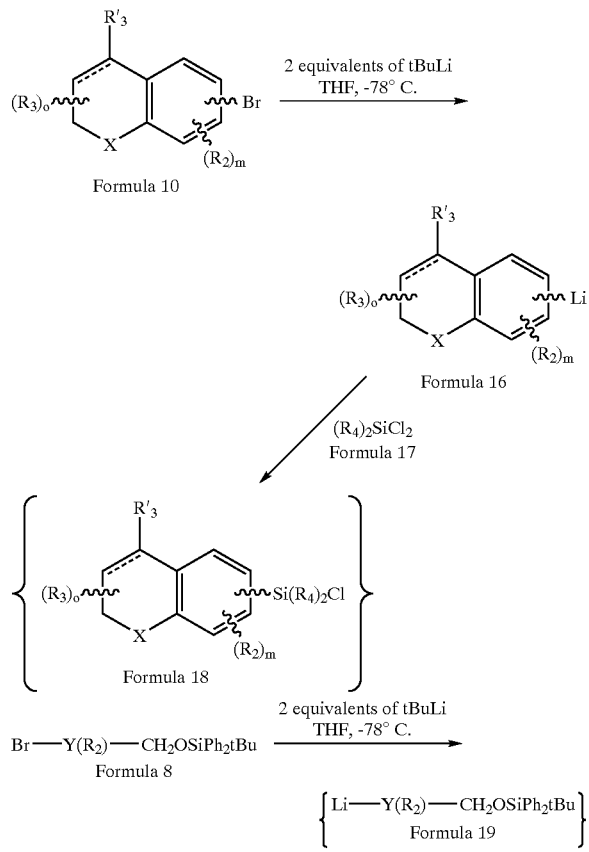

-continued

Formula 18 + Formula 19

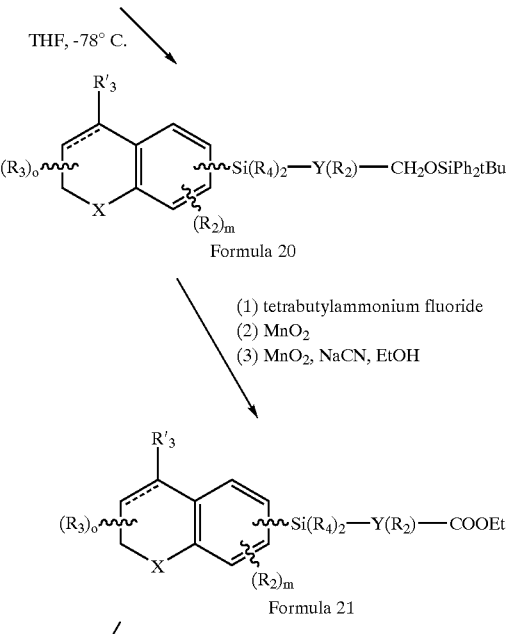

Formula 20

(1) tetrabutylammonium fluoride
(2) MnO₂
(3) MnO₂, NaCN, EtOH

Formula 21

HOMOLOGS AND DERIVATIVES

The starting compounds utilized in Reaction Scheme 2 are the condensed cyclic bromoaryl compounds of Formula 10, which have been described above in connection with Reaction Scheme 1, and 1a. The bromo aryl compounds of Formula 10 are converted into an organometallic, preferably, organolithium reagent, as is shown in Scheme 2. Exchange of the bromine (or of iodine if an iodoaryl reagent is used) with lithium is conducted under conditions normally practiced in the art, typically with two equivalents of tert-butyl lithium, in an ethereal reagent (THF) in the cold, typically −78° F. The resulting condensed cyclic aryl lithium reagent of Formula 16 is then reacted with a dialkyldichlorosilane, alkylphenyldichlorosilane or diphenyldichlorosilane reagent of Formula 17. The $R_4$ groups in Formula 17 have the same definition as in connection with Formulas 1–4. The dialkyldichlorosilane, alkylphenyldichlorosilane or diphenyldichlorosilane reagents are available commercially, or can be prepared in accordance with known procedures within the skill of the ordinary practitioner in the field.

As is shown in Reaction Scheme 2, with the bromoaryl compound of Formula 10 the $(R_4)_2SiCl_2$ reagent forms an aryl dialkylchlorosilane of Formula 18. The latter is typically not isolated, but used without isolation to react with an organolithium compound of Formula 19 that is also prepared by bromine—lithium exchange from the (bromoaryl)methyl t-butyldiphenylsilyl ether of Formula 8, described above in connection with Reaction Scheme 1. The (aryl)methyl t-butyldiphenylsilyl ether lithium reagent of Formula 19 is also typically not isolated before reacting it with the reagent of Formula 18. This is indicated in the reaction scheme by placing the reagents of Formulas 18 and 19 in large square brackets.

The product of the reaction between the aryl dialkylchlorosilane of Formula 18 and the (aryl)methyl t-butyldiphenylsilyl ether lithium reagent of Formula 19 is the diarylsilane compound of Formula 20 that still has the tert-butyldiphenylsilyl protecting group on the primary alcohol function. This is removed by treatment with tetrabutylammonium fluoride, and the resulting primary alcohol can be oxidized to the ester stage (Formula 21) in analogy to the reactions described in connection with Reaction Scheme 1. The diarylsilane compounds of Formula 21 are within the scope of the invention, particularly within the scope of Formula 1 and can be converted into further homologs and derivatives, as described above. A particularly preferred step of such conversion is scarification of the ester group with base to provide the free carboxylic acids (or salts thereof) of the invention.

The diarylsilane compounds of Formula 2 can be prepared in analogy to the preparation of the diarylsilane compounds of Formula 1. A starting material in this synthetic route is a halogenated benzene derivative, such as bromobenzene, iodobenzene or a substituted derivative thereof where the substituent is $R_2$.

REACTION SCHEME 3

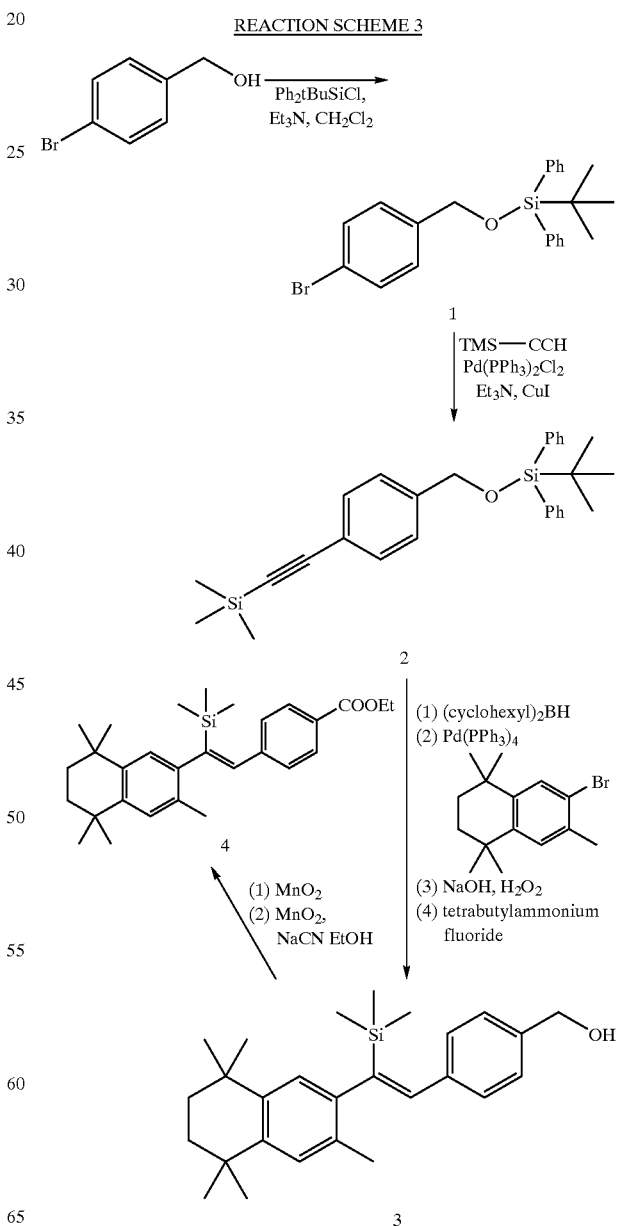

REACTION SCHEME 4

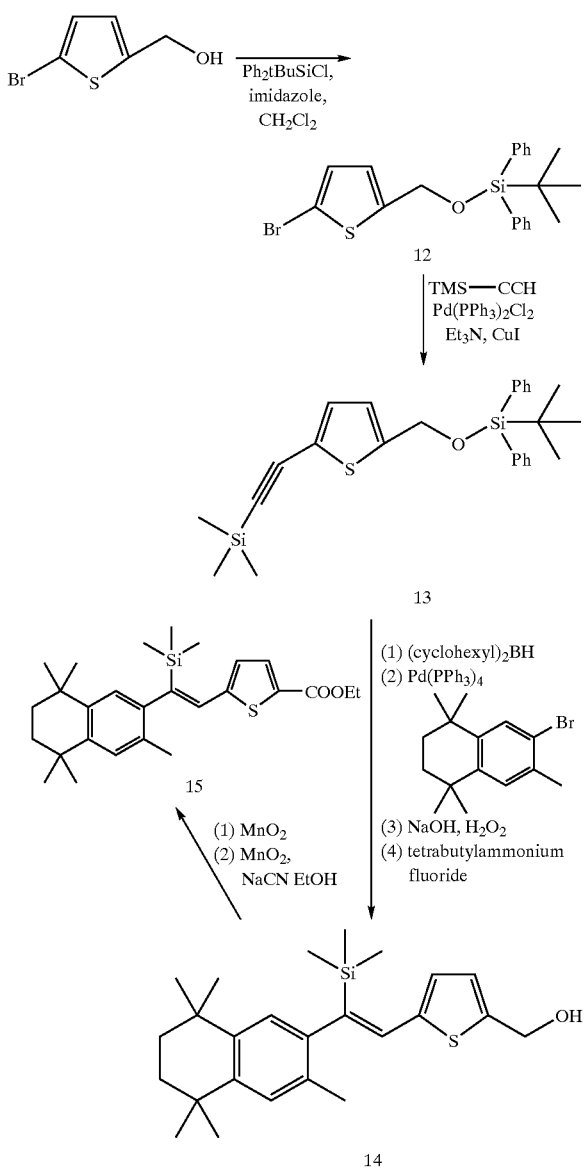

Reaction Schemes 3 and 4 illustrate the synthesis of certain exemplary compounds of the invention. The synthetic processes illustrated in these two schemes are described in detail in the section titled "Specific Chemical Examples" below.

SPECIFIC CHEMICAL EXAMPLES

4-Bromobenzyl tert-butyldiphenylsilyl Ether (Compound 1)

Tert-butyldiphenylsilyl chloride (10.4 mL, 40.1 mmol) was added to a solution of 4-bromobenzyl alcohol ( 5.0 g, 26.7 mmol) and 50 mL of dichloromethane. The solution was treated with triethylamine (3.72 mL, 26.7 mmol) and (dimethylamino)pyridine (163 mg, 1.34 mmol) and stirred overnight at room temperature. The solution was diluted with 300 mL of dichloromethane and washed with 50 mL of 10% aqueous HCl. The layers were separated and the aqueous layer was extracted with 50 mL of dichloromethane. The combined organic extracts were washed with brine, and dried (MgSO$_4$), and filtered, and the solvents were removed in vacuo. The residue was filtered through a plug (6@X 2@) of silica gel using a solution of 97% hexane/ethyl acetate. After removal of the solvent the residue was heated under vacuum (3 torr) to 170° C. for 1 hour to remove a low-boiling impurity. The remaining material is the title compound.

PNMR (300 MHz, CDCl$_3$).1.09 (s, 9 H), 4.70 (s, 2 H), 7.20 (d, 2 H, J=7.9 Hz), 7.35–7.45 (m, 8 H), 7.65 (overlapping ds, 4 H).

4-[(trimethylsilyl)ethynyl]benzyl tert-butyldiphenylsilyl Ether (Compound 2)

A 25 mL round bottom flask was flame-dried under high vacuum. The vacuum was broken by the addition of dry argon, and the flask was allowed to cool to room temperature. The flask was charged with 2.0 g (4.70 mmol) of 4-bromobenzyl tert-butyldiphenylsilyl ether (Compound 1), 2.0 mL (14.1 mmol) of (trimethylsilyl)acetylene, and 16.5 mL of triethylamine. The solution was purged with argon for 15 minutes and bis(triphenylphosphine)palladium (II) chloride (83 mg, 0.12 mmol) and copper (I) iodide (22 mg, 0.12 mmol) were added and the solution stirred at ambient temperature for 3 days. The solution was poured into a separatory funnel containing water and ether. The layers were separated and the aqueous layer was extracted 3 times with ether. The combined ether layers were washed once with brine, and dried over magnesium sulfate, and the solvents were removed under reduced pressure. The residue was purified by distillation (bp=180° B 185° C., 1 torr) to give the title compound.

PNMR (300 MHz, CDCl$_3$).0.23 (s, 9 H), 1.09 (s, 9 H), 4.73 (s, 2 H), 7.23 (d, 2 H, J=7.9 Hz), 7.31–7.45 (m, 8 H), 7.65 (overlapping ds, 4 H).

(Z)-4-[2-(3,5,5,8,8-Pentamethyl-5,6,7,8-tetrahydronaphthalen-2-yl)-2-(trimethylsilyl)vinyl]benzyl Alcohol (Compound 3) General Procedure A A 3-neck 25 mL round bottom flask was fitted with a reflux condenser, and flame-dried under high vacuum. The vacuum was broken by the addition of dry argon (3×), and the flask was allowed to cool to room temperature. The flask was charged with 0.5 mL (1.0 mmol) of borane-methyl sulfide and THF (0.3 mL) and cooled to 0° C. The solution was treated with 0.20 mL (2 mmol) of cyclohexene and stirred at 0° C. for 1 hour. Neat 4-[(trimethylsilyl)ethynyl] benzyl tert-butyldiphenylsilyl ether (Compound 2, 443 mg, 1 mmol) was added and, after 15 minutes the solution was warmed to room temperature and stirred for 2.25 hours. In a second flask was prepared a solution of tetrakis (triphenylphosphine)palladium (0) (58 mg, 0.05 mmol) and 2-bromo-3,5,5,8,8-pentamethyl-5,6,7,8-tetrahydronaphthalene (1.26 g, 4.5 mmol) in 5 mL of THF, which was purged with argon for 10 minutes. The solvents in the first flask were removed under high vacuum, and the residue dissolved in 1 mL of THF and 1 mL of 2 M aqueous NaOH, and the resulting solution was purged with argon for 10 minutes. A 1 mL aliquot of the solution from the second flask was added to the first flask, and the reaction was protected from light and refluxed for 5 hours. The reaction was cooled to room temperature and treated with 2 M NaOH (1 mL) and 30% hydrogen peroxide (0.4 mL). The solution was poured into a separatory funnel containing water and pentane. The layers were separated and the aqueous layer was extracted 3 times with pentane. The combined organic layers were washed once with brine, and dried over magnesium sulfate, and the solvents were removed under reduced pressure. The residue was partially purified by silica gel chromatograhy (99:1, hexane:ethyl acetate). The later fractions were combined and concentrated under reduced pressure. The residue (203 mg) was dissolved in 3.2 mL of THF and treated with 313 mg of tetrabutylammonium flouride (Tbaf) adsorbed onto silica gel (1.6 mmol flouride per gram). The suspension was stirred for 5 hours at room temperature and then the silica gel was washed with ether, and the separated ether extracts were dried over magnesium sulfate. The filtered solvents were removed under reduced pressure and the residue purified by silica gel chromatography (4:1, hexane:ethyl acetate) to give the title compound.

PNMR (300 MHz, CDCl$_3$).−0.10 (s, 9 H), 1.29 (s, 12 H), 1.68 (s, 4 H), 2.24 (s, 3 H), 4.72 (s, 2 H), 6.87 (s, 1 H), 7.07 (s, 1 H), 7.17 (s, 1 H), 7.35 (s, 4 H).

Ethyl (Z)4-[2-(3,5,5,8,8-pentamethyl-5,6,7,8-tetrahydronaphthalen-2-yl)-2-(trimethylsilyl)vinyl] benzoate (Compound 4) General Procedure B Manganese dioxide (265 mg, 2.96 mmol) was added to a solution of (Z)-4-[2-(3,5,5,8,8-pentamethyl-5,6,7,8-tetrahydronaphthalen-2-yl)-2-(trimethylsilyl)vinyl]benzyl alcohol (Compound 3, 60 mg, 0.15 mmol) and 3.65 mL of hexane. The solution was stirred at room temperature for 16 hours, the manganese dioxide filtered off, and the hexane removed in vacuo. The residue was dissolved in 2 mL of ethanol and treated with sodium cyanide (37.5 mg, 0.77 mmol) and acetic acid (13.7 mg, 0.23 mmol). After 15 minutes, the solution was treated with 265 mg (3.0 mmol) of manganese dioxide. The suspension was stirred at room temperature for 6 hours and the manganese dioxide removed by filtration. The solution was poured into a separatory funnel containing water and ether. The layers were separated and the aqueous layer was extracted 3 times with ether. The combined organic layers were washed once with brine, and dried over magnesium sulfate, and the solvents were removed under reduced pressure. The residue was purified by silica gel chromatograhy (97:3, hexane:ethyl acetate) to give the title compound. PNMR (300 MHz, CDCl$_3$).−0.11 (s, 9 H), 1.28 (s, 12 H), 1.41 (t, 3 H, J=7.1 Hz), 1.68 (s, 4 H), 2.23 (s, 3 H), 4.39 (q, 2 H, J=7.1 Hz), 6.86 (s, 1 H), 7.08 (s, 1 H), 7.17 (s, 1 H), 7.41 (d, 2 H, J=8.5 Hz), 8.03 (d, 2 H, J=8.5 Hz).

(Z)-4-[2-(3,5,5,8,8-Pentamethyl-5,6,7,8-tetrahydronaphthalen-2-yl)-2-(trimethylsilyl)vinyl] benzoic Acid (Compound 5) General Procedure C To a solution of ethyl (Z)-4-[2-(3,5,5,8,8-pentamethyl-5,6,7,8-tetrahydronaphthalen-2-yl)-2-(trimethylsilyl)vinyl] benzoate (Compound 4, 0.034 g, 0.076 mmol) and 2 mL of ethyl alcohol was added aqueous 1 N KOH (0.5 mL). The resulting solution was heated in an 50° C. bath until the hydrolysis reaction was completed, as judged by thin layer chromatography. The solution was cooled to room temperature, diluted with water and washed once with 1:1 ether:hexane solution, and the layers were separated. The aqueous layer was acidified with 1 N aqueous HCl and the product extracted 3 times with ethyl acetate. The combined organic extracts were washed with brine, and dried over MgSO$_4$, and filtered, and the solvents were removed in vacuo to give the title compound as a white solid.

PNMR (300 MHz, CDCl$_3$). −0.09 (s, 9 H), 1.28 (s, 12 H), 1.68 (s, 4 H), 2.24 (s, 3 H), 6.86 (s, 1 H), 7.08 (s, 1 H), 7.18 (s, 1 H), 7.46 (d, 2 H, J=8.1 Hz), 8.11 (d, 2 H, J=8.1 Hz).

(Z)-4-[2-(5,5,8,8-Tetramethyl-5,6,7,8-tetrahydronaphthalen-2-yl)-2-(trimethylsilyl)vinyl] benzyl Alcohol (Compound 6)

Following General Procedure A, 4-[(trimethylsilyl) ethynyl]benzyl tert-butyldiphenylsilyl ether (Compound 2, 0.89 g, 2.0 mmol) and 2-bromo-5,5,8,8-tetramethyl-5,6,7,8-tetrahydronaphthalene (0.60 g, 2.25 mmol) were coupled to give the title compound. 2-bromo-5,5,8,8-tetramethyl-5,6,7, 8-tetrahydronaphthalene can be prepared in accordance with the procedure set forth in J. Med. Chem. 34:2930–41 (1994). The pentamethyl derivative thereof can be prepared in accordance with the same procedure.

PNMR (300 MHz, CDCl$_3$).−0.05 (s, 9 H), 1.30 (s, 6 H), 1.32 (s, 6 H), 1.70 (s, 4 H), 4.72 (s, 2 H), 6.97 (dd, 1 H, J=2.0, 8.1 Hz), 7.10 (d, 1 H, J=2.0 Hz), 7.24 (d, 1 H, J=8.1 Hz), 7.28 (s, 1 H), 7.33 (s, 4 H).

Ethyl (Z)-4-[2-(5,5,8,8-tetramethyl-5,6,7,8-tetrahydronaphthalen-2-yl)-2-(trimethylsilyl)vinyl] benzoate (Compound 7)

Following General Procedure B, (Z)-4-[2-(5,5,8,8-tetramethyl-5,6,7,8-tetrahydronaphthalen-2-yl)-2-(trimethylsilyl)vinyl]benzyl alcohol (Compound 6, 0.50 g, 1.3 mmol) was oxidized to give the title compound.

PNMR (300 NMz, CDCl$_3$).−0.05 (s, 9 H), 1.29 (s, 6 H), 1.31 (s, 6 H), 1.41 (t, 3 H, J=7.1 Hz), 1.69 (s, 4 H), 4.39 (d, 2 H, J=7.1 Hz), 6.95 (dd, 1 H, J=2.0, 8.1 Hz), 7.09 (d, 1 H, J=2.0 Hz), 7.24 (d, 1 H, J=8.1 Hz), 7.27 (s, 1 H), 7.38 (d, 2 H, J=8.3 Hz), 8.02 (d, 2 H, J=8.3 Hz).

(Z)-4-[2-(5,5,8,8-Tetramethyl-5,6,7,8-tetrahydronaphthalen-2-yl)-2-(trimethylsilyl)vinyl] benzoic Acid (Compound 8)

Following General Procedure C, ethyl (Z)-4-[2-(5,5,8,8-tetramethyl-5,6,7,8-tetrahydronaphthalen-2-yl)-2-(trimethylsilyl)vinyl]benzoate (Compound 7, 0.205 g, 0.47 mmol) was hydrolyzed to give the title compound.

PNMR (300 MHz, CDCl$_3$) −0.04 (s, 9 H), 1.29 (s, 6 H), 1.32 (s, 6 H), 1.70 (s, 4 H), 6.97 (dd, 1 H, J=2.0, 8.1 Hz), 7.09 (d, 1 H, J=2.0 Hz), 7.25 (d, 1 H, J=8.1 Hz), 7.29 (s, 1 H), 7.43 (d, 2 H, J=8.1 Hz), 8.09 (d, 2 H, J=8.1 Hz).

Ethyl 4-[(trimethylsilyl)ethynyl]benzoate (Compound 9)

A resealable tube was flame-dried under high vacuum. The vacuum was broken by the addition of dry argon, and the flask was allowed to cool to room temperature. The flask was charged with 5.0 g (18.1 mmol) of ethyl 4-bromobenzoate, 7.7 mL (54.3 mmol) of (trimethylsilyl) acetylene, and 65 mL of diethylamine. The solution was purged with argon for 15 minutes and bis (triphenylphosphine)palladium (II) chloride (320 mg, 0.45 mmol) and copper (I) iodide (87 mg, 0.45 mmol) were added, the tube sealed, and the solution stirred at 55° C. for 3 days. The solution was poured into a separatory funnel containing water and ether. The layers were separated and the aqueous layer was extracted 3 times with ether. The combined ether layers were washed once with brine, and dried over magnesium sulfate, and the solvents were removed under reduced pressure. The residue was purified by silica gel chromatography (95:5. hexane:ethyl acetate) to give the title compound.

PNMR (300 MHz, CDCl$_3$).0.26 (s, 9 H), 1.39 (t, 3 H, J=7.1 Hz), 4.36 (q, 2 H, J=7.1 Hz), 7.51 (d, 2 H, J=8.6 Hz), 7.97 (d, 2 H, J=8.6 Hz).

Ethyl (Z)-4-[2-(2,2,4,4-tetramethylchroman-6-yl)-2-(trimethylsilyl)vinyl]benzoate (Compound 10)

Following General Procedure A, ethyl 4-[(trimethylsilyl) ethynyl]benzoate (Compound 9, 0.51 g, 2.0 mmol) and 6-bromo-2,2,4,4-tetramethylchroman (0.57 g, 2.25 mmol) were coupled to give the title compound.

PNMR (300 MHz, CDCl$_3$).−0.06 (s, 9 H), 1.36 (s, 6 H), 1.37 (s, 6 H), 1.39 (t, 3 H, J=7.1 Hz), 1.85 (s, 2 H), 4.38 (q, 2 H, J=7.1 Hz), 6.75 (d, 1 H, J=8.3 Hz), 6.94 (dd, 1 H, J=2.3, 8.3 Hz), 7.07 (s, 1 H), 7.26 (d, 1 H, J=2.3 Hz), 7.38 (d, 2 H, J=7.9 Hz), 8.02 (d, 2 H, J=7.9 Hz).

(Z)-4-[2-(2,2,4,4-Tetramethylchroman-6-yl)-2-(trimethylsilyl)vinyl]benzoic Acid (Compound 11)

Following General Procedure C, ethyl (Z)-4-[2-(2,2,4,4-tetramethylchroman-6-yl)-2-(trimethylsilyl)vinyl]benzoate (Compound 10, 0.48 g, 1.1 mmol) was hydrolyzed to give the title compound.

PNMR (300 MHz, CDCl$_3$).−0.04 (s, 9 H), 1.37 (s, 6 H), 1.39 (s, 6 H), 1.86 (s, 2 H), 6.76 (d, 1 H, J=8.3 Hz), 6.94 (dd, 1 H, J=2.2, 8.3 Hz), 7.09 (d, 1 H, J=2.2 Hz), 7.29 (s, 1 H), 7.44 (d, 2 H, J=8.2 Hz), 8.11 (d, 2 H, J=8.2 Hz).

(5-Bromothiophen-2-yl)methyl Tert-butyldiphenylsilyl Ether (Compound 12)

Tert-butyldiphenylsilyl chloride (7.8 mL, 30.1 mmol) was added to a solution of 5-bromo(thiophen-2-yl)methyl alcohol (4.9 g, 25.1 mmol) and 9.7 mL of dimethylformamide. The solution was treated with imidazole (4.29 g, 62.8 mmol) and stirred overnight at room temperature. The solution was diluted with ether and washed with 2% aqueous HCl. The layers were separated and the aqueous layer was extracted with ether. The combined organic extracts were washed with brine, and dried (MgSO$_4$), and filtered, and the solvents were removed in vacuo. The residue was purified by silica gel chromatography (hexane) to produce the title compound.

PNMR (300 MHz, CDCl$_3$).1.10 (s, 9 H), 4.80 (s, 2 H), 6.56 (d, 1 H, J=2.4 Hz), 6.88 (d, 1 H, J=2.4 Hz), 7.38–7.50 (m, 8 H), 7.70 (m, 4 H).

5-[(Trimethylsilyl)ethynyl]thiophen-2-ylmethyl Tert-butyldiphenylsilyl Ether (Compound 13)

A round bottom flask was flame-dried under high vacuum. The vacuum was broken by the addition of dry argon, and the flask was allowed to cool to room temperature. The flask was charged with 2.16 g (5.0 mmol) of (5-bromothiophen-2-yl)methyl tert-butyldiphenylsilyl ether (Compound 12), 2.12 mL (15 mmol) of (trimethylsilyl)acetylene, and 17.5 mL of triethylamine. The solution was purged with argon for 15 min and bis(triphenylphosphine)palladium (II) chloride (88 mg, 0.125 mmol) and copper (I) iodide (24 mg, 0.125 mmol) were added and the solution stirred at ambient temperature for 3 days. The solution was poured into a separatory funnel containing water and ether. The layers were separated and the aqueous layer was extracted 3 times with ether. The combined ether layers were washed once with brine, and dried over magnesium sulfate, and the solvents were removed under reduced pressure. The residue was purified by silica gel chromatography (hexane) to give the title compound.

PNMR (300 MHz, CDCl$_3$).0.25 (s, 9 H), 1.08 (s, 9 H), 4.83 (s, 2 H), 6.63 (d, 1 H, J=3.8 Hz), 7.06 (d, 1 H, J=3.8 Hz), 7.41 (m, 8 H), 7.68 (overlapping ds, 4 H).

(Z)-5-[2-(3,5,5,8,8-Pentamethyl-5,6,7,8-tetrahydronaphthalen-2-yl)-2-(trimethylsilyl)vinyl] thiophene-2-ylmethyl Alcohol (Compound 14)

Following General Procedure A, 5-[(trimethylsilyl) ethynyl]thiophen-2-ylmethyl tert-butyldiphenylsilyl Ether (Compound 13, 0.75 g, 1.8 mmol) and 2-bromo-3,5,5,8,8-pentamethyl-5,6,7,8-tetrahydronaphthalene (0.45 g, 1.67 mmol) were coupled to give the title compound.

PNMR (300 MHz, CDCl$_3$).−0.2 (s, 9 H), 1.42 (s, 6 H), 1.43 (s, 6 H), 1.83 (s, 4 H), 2.34 (s, 3 H), 4.95 (s, 2 H), 6.97 (s, 1 H), 7.04 (s, 2 H), 7.19 (s, 1 H), 7.21 (s, 1 H).

Ethyl (Z)-5-[2-(3,5,5,8,8-pentamethyl-5,6,7,8-tetrahydronaphthalen-2-yl)-2-(trimethylsilyl)vinyl] thiophene-2-carboxylate (Compound 15)

Following General Procedure B, (Z)-5-[2-(3,5,5,8,8-pentamethyl-5,6,7,8-tetrahydronaphthalen-2-yl)-2-(trimethylsilyl)vinyl]thiophene-2-ylmethyl alcohol (Compound 14, 0.088 g, 0.213 mmol) was oxidized to give the title compound.

PNMR (300 MHz, CDCl$_3$).−0.029 (s, 9 H), 1.26 (s, 6 H), 1.27 (s, 6 H), 1.39 (t, 3 H, J=7.1 Hz), 1.67 (s, 4 H), 2.17 (s, 3 H), 4.35 (q, 2 H, J=7.1 Hz), 6.80 (s, 1 H), 7.00 (d, 1 H, J=3.8 Hz), 7.02 (s, 1 H), 7.06 (s, 1 H), 7.69 (d, 1 H, J=3.8 Hz).

(Z)-5-[2-(3,5,5,8,8-Pentamethyl-5,6,7,8-tetrahydronaphthalen-2-yl)-2-(trimethylsilyl)vinyl] thiophene-2-carboxylic Acid (Compound 16)

Following General Procedure C, ethyl (Z)-5-[2-(3,5,5,8, 8-pentamethyl-5,6,7,8-tetrahydronaphthalen-2-yl)-2-(trimethylsilyl)vinyl]thiophene-2-carboxylate (Compound 15, 0.050 g, 0.11 mmol) was hydrolyzed to give the title compound.

PNMR (300 MHz, CDCl$_3$).0.04 (s, 9 H), 1.26 (s, 6 H), 1.27 (s, 6 H), 1.67 (s, 4 H), 2.18 (s, 3 H), 7.02 (s, 1 H), 7.04 (s, 1 H), 7.05 (d, 1 H, J=4.1 Hz), 7.26 (s, 1 H), 7.79 (d, 1 H, J=4.1 Hz).

(Z)-5-[2-(5,5,8,8-Tetramethyl1–5,6,7,8-tetrahydronaphthalen-2-yl)-2-(trimethylsilyl)vinyl] thiophene-2-ylmethyl Alcohol (Compound 17)

Following General Procedure A, 5-[(trimethylsilyl) ethynyl]thiophen-2-ylmethyl tert-butyldiphenylsilyl ether (Compound 13, 0.75 g, 1.8 mmol) and 2-bromo-5,5,8,8-tetramethyl-5,6,7,8-tetrahydronaphthalene (0.46 g, 1.62 mmol) were coupled to give the title compound.

PNMR (300 MHz, CDCl$_3$).0.2 (s, 9 H), 1.42 (s, 6 H), 1.43 (s, 6 H), 1.83 (s, 4 H), 4.95 (s, 2 H), 6.97 (s, 1 H), 7.04 (s, 2 H), 7.19 (s, 1 H), 7.21 (s, 1 H).

Ethyl (Z)-5-[2-(5,5,8,8-tetramethyl-5,6,7,8-tetrahydronaphthalen-2-yl)-2-(trimethylsilyl)vinyl]thiophene-2-carboxylate (Compound 18)

Following General Procedure B, (Z)-5-[2-(3,5,5,8,8-tetramethyl-5,6,7,8-tetrahydronaphthalen-2-yl)-2-(trimethylsilyl)vinyl]thiophene-2-ylmethyl alcohol (Compound 17, 0.30 g, 0.753 mmol) was oxidized to give the title compound.

PNMR (300 MHz, CDCl$_3$).−0.029 (s, 9 H), 1.26 (s, 6 H), 1.27 (s, 6 H), 1.39 (t, 3 H, J=7.1 Hz), 1.67 (s, 4 H), 4.35 (q, 2 H, J=7.1 Hz), 6.80 (s, 1 H), 7.00 (d, 1 H, J=3.8 Hz), 7.02 (s, 1 H), 7.06 (s, 1 H), 7.69 (d, 1 H, J=3.8 Hz).

(Z)-5-[2-(5,5,8,8-Tetramethyl-5,6,7,8-tetrahydronaphthalen-2-yl)-2-(trimethylsilyl)vinyl]thiophene-2-carboxylic Acid (Compound 19)

Following General Procedure C, ethyl (Z)-5-[2-(5,5,8,8-tetramethyl-5,6,7,8-tetrahydronaphthalen-2-yl)-2-(trimethylsilyl)vinyl]thiophene-2-carboxylate (Compound 18, 0.125 g, 0.284 mmol) was hydrolyzed to give the title compound.

PNMR (300 MHz, CDCl$_3$).−0.04 (s, 9 H), 1.26 (s, 6 H), 1.27 (s, 6 H), 1.67 (s, 4 H), 7.02 (s, 1 H), 7.04 (s, 1 H), 7.05 (d, 1 H, J=4.1 Hz), 7.26 (s, 1 H), 7.79 (d, 1 H, J=4.1 Hz).

4-[Diethyl(5,5,8,8-tetramethyl-5,6,7,8-tetrahydronaphthalen-2-yl)silyl]benzyl Alcohol (Compound 20)

To a −78° C. solution of 2-bromo-5,5,8,8-tetramethyl-5,6,7,8-tetrahydronaphthalene (1.34 g, 5.0 mmol) in 6.9 mL of THF was added n-butyllithium (1.6 M, 3.13 mL, 5.0 mmol). After ten minutes, the solution was added via cannula to a B78° C. solution of diethyldichlorosilane (0.61 mL, 5.0 mmol) and THF (4.4 mL) and stirring continued for 1 hour. In a second flask containing 4-bromobenzyl tert-butyldiphenylsilyl ether (Compound 1, 3.19 g, 7.5 mmol) and THF (2 mL) at −78° C. was added n-butyllithium (1.6 M, 4.69 mL, 7.5 mmol). After ten minutes, the contents of the second flask were added via canula to the first flask. After 30 minutes at −78° C., the reaction was quenched by the addition of 5 mL of saturated aqueous NH$_4$Cl. The solution was poured into a separatory funnel containing water and hexane. The layers were separated and the aqueous layer was extracted 3 times with hexane. The combined organic layers were washed once with brine, and dried over magnesium sulfate, and the solvents were removed under reduced pressure. The residue was dissolved in 20 mL of THF and treated with 3.2 g of tetrabutylammonium flouride (Tbaf) adsorbed onto silica gel (1–1.6 mmol flouride per gram). The suspension was stirred for 5 hours at room temperature and then the silica gel was washed with ether, and the separated ether extracts were dried over magnesium sulfate. The filtered solvents were removed under reduced pressure and the residue purified by silica gel chromatography (9:1, hexane:ethyl acetate) to give the title compound.

PNMR (300 MHz, CDCl$_3$).0.91–1.06 (m, 10 H), 1.25 (s, 6 H), 1.28 (s, 6 H), 1.68 (s, 4 H), 4.70 (s, 2 H), 7.22–7.25 (overlapping ds, 2 H), 7.35 (d, 2 H, J=8.1 Hz), 7.44 (s, 1 H), 7.53 (d, 1 H, J=8.1 Hz).

Ethyl 4-[diethyl(5,5,8,8-tetramethyl-5,6,7,8-tetrahydronaphthalen-2-yl]silylbenzoate (Compound 21)

Following General Procedure B, 4-[diethyl(5,5,8,8,-tetramethyl-5,6,7,8

Compound 21

-tetrahydronaphthalen-2-yl]silylbenzyl alcohol (Compound 20, 1.25 g, 3.30 mmol) was oxidized to give the title compound.

PNMR (300 MHz, CDCl$_3$).0.99–1.09 (m, 10 H), 1.24 (s, 6 H), 1.28 (s, 6 H), 1.39 (t, 3 H, J=7.1 Hz), 1.67 (s, 4 H), 4.37 (q, 2 H, J=7.1 Hz), 7.22–7.29 (overlapping ds, 2 H), 7.42 (s, 1 H), 7.60 (d, 2 H, J=8.1 Hz), 8.00 (d, 1 H, J=8.1 Hz).

4-[Diethyl(5,5,8,8-tetramethyl-5,6,7,8-tetrdronaphthalen-2-yl]silylbenzoic Acid (Compound 22)

Compound 22

Following General Procedure C, ethyl 4-[diethyl(5,5,8,8-tetramethyl-5,6,7,8-tetrahydronaphthalen-2-yl]silylbenzoate (Compound 21, 0.650 g, 1.54 mmol) was hydrolyzed to give the title compound.

PNMR (300 MHz, CDCl$_3$).0.99–1.10 (m, 10 H), 1.25 (s, 6 H), 1.28 (s, 6 H), 1.68 (s, 4 H), 7.22–7.30 (overlapping ds, 2 H), 7.42 (s, 1 H), 7.64 (d, 2 H, J=8.1 Hz), 8.07 (d, 1 H, J=8.1 Hz).

4-[(Z)-(5.5-Dimethyl-8-p-tolyl-5,6-dihydronaphthalen-2-yl)trimethylsilanylvinyl]-benzyl Alcohol (Compound 23).

Compound 23

Following General Procedure A, 4-[(trimethylsilyl)ethynyl]benzyl tert-butyldiphenylsilyl ether and 6-bromo-1,1-dimethyl-4-p-tolyl-1,2-dihydronaphthalene (prepared as described in Klein, et al., U.S. Pat. No. 5,952,345) were coupled to give the title compound (Compound 23). PNMR (300 MHz, CDCl$_3$): δ0.13 (s, 9 H), 1.47 (s, 6 H), 2.48 (d, J=4.4 Hz, 2 H), 2.54 (s, 3 H), 4.82 (d, J=6.1 Hz, 2 H), 6.10 (t, J=4.4 Hz, 1 H), 7.00 (d, J=2.2 Hz, 1 H), 7.18 (dd, J=2.2, 7.9 Hz, 1 H), 7.30–7.45 (m, 10 H).

Ethyl (Z)-4-[(5,5-Dimethyl-8-p-tolyl-5,6-dihydronaphthalen-2-yl)trimethylsilanyl-vinyl]benzoate. (Compound 24)

Compound 24

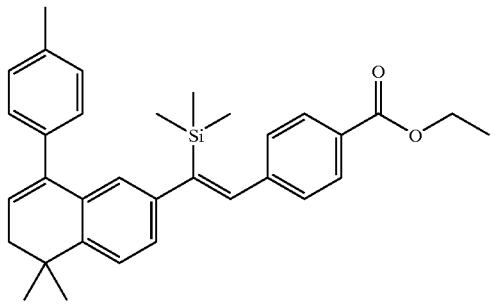

Following General Procedure B, 4-[(Z)-(5,5-dimethyl-8-p-tolyl-5,6-dihydronaphthalen-2-yl)trimethylsilanylvinyl] benzyl alcohol was oxidized to give the title compound (Compound 24). PNMR (300 MHz, CDCl$_3$): (Compound 34) 0.0 (s, 9 H), 1.47 (s, 6 H), 1.53 (t, J=7.0 Hz, 3 H), 2.48 (d, J=4.7 Hz, 2 H), 2.54 (s, 3 H), 4.50 (q, J=7.0 Hz, 2 H), 6.10 (t, J=4.7 Hz, 1 H), 6.99 (d, J=2.0 Hz 1 H), 7.17 (dd, J=2.0, 7.9 Hz, 1 H), 7.30–7.54 (m, 8 H), 8.11 (d, J=8.2 Hz, 2 H).

(Z)-4-[(5,5-Dimethyl-8-p-tolyl-5,6-dihydronaphthalen-2-yl)trimetheylsilanylvinyl]-benzoic Acid.(Compound 25)

Compound 25

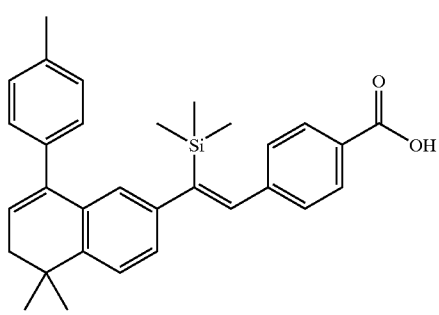

Following General Procedure C, ethyl (Z)-4-[(5,5-dimethyl-8-p-tolyl-5,6-dihydronaphthalen-2-yl) trimethylsilanylvinyl]benzoate was hydrolyzed to give the title compound (Compound 25). PNMR (300 MHz, CDCl$_3$): δ0.0 (s, 9 H), 1.47 (s, 6 H), 2.48 (d, J=4.9 Hz, 2 H), 2.54 (s, 3 H), 6.10 (t, J=4.9 Hz, 1 H), 6.98 (d, J=2.0 Hz, 1 H), 7.16 (dd, J=2.0, 7.9 Hz, 1 H), 7.30–7.60 (m, 8 H), 8.15 (d, J=8.3 Hz,2 H).

(Z)-{4-(5,5-Dimethyl-8-phenyl-5,6-dihydronaphthalen-2-yl)trimethelsilanylvinyl]-benzyl Alcohol.(Compound 26).

Compound 26

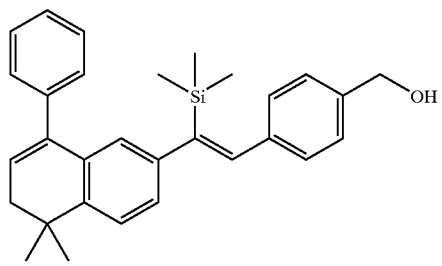

Following General Procedure A, 4-[(trimethylsilyl) ethynyl]benzyl030 tert-butyldiphenylsilyl ether and 6-bromo-1,1-dimethyl-4-phenyl-1,2-dihydronaphthalene (which can be prepared by the procedure described in Klein, et al., U.S. Pat. No. 5,952,345) were coupled to give the title compound (Compound 26). PNMR (300 MHz, CDCl$_3$): δ0.0 (s, 9 H), 1.49 (s, 6 H), 2.50 (d, J=4.4 Hz, 2 H), 4.80 (d, J=5.7 Hz, 2 H), 6.13 (t, J=4.4 Hz, 1 H), 6.98 (d, J=2.2 Hz, 1 H), 7.21 (dd, J=2.2, 7.9 Hz, 1 H), 7.31–7.60 (m, 7 H).

Ethyl (Z)-4-[(5,5-Dimethyl-8-phenyl-5,6-dihydronaphthalen-2-yl)trimethylsilanyl-vinyl] benzoate.(Compound 27)

Compound 27

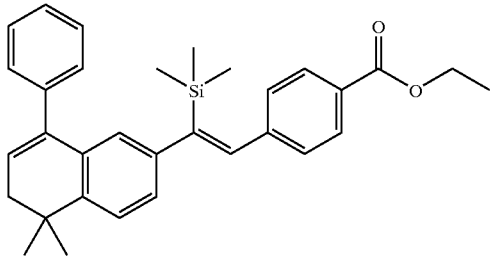

Following General Procedure B, (Z)-4-[(5,5-dimethyl-8-phenyl-5,6-dihydronaphthalen-2-yl)trimethylsilanylvinyl] benzyl alcohol was oxidized to give the title compound (Compound 27). PNMR (300 MHz, CDCl$_3$): δ0.0 (s, 9 H), 1.50 (s, 6 H), 1.55 (t, J=Q7.4 Hz, 3 H), 2.51 (d, J=4.8 Hz, 2 H), 4.52 (q, J=7.4 Hz, 2 H),6.15 (t, J=4.8 Hz, 1 H), 6.99 (d, J=2.2 Hz, 1 H), 7.21 (dd, J=2.2, 7.9 Hz, 1 H), 7.33 (s, 1 H),7.40–7.60 (m, 7 H), 8.12 (d, J=8.3 Hz, 2 H).

(Z)-4-[(5,5-Dimethyl-8-phenyl-5,6-dihydronaphthalen-2-yl)trimethylsilanylvinyl]-benzoic Acid.(Compound 28)

Compound 28

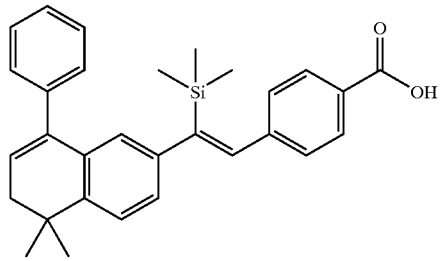

Following General Procedure C, ethyl (Z)-4-[(5,5-dimethyl-8-phenyl-5,6-dihydronaphthalen-2-yl)trimethylsilanylvinyl]benzoate was hydrolyzed to give the title compound (Compound 28). PNMR (300 MHz, CDCl$_3$): δ0.13 (s, 9 H), 1.49 (s, 6 H), 2.50 (d, J=4.9 Hz, 2 H), 6.13 (t, J=4.9 Hz, 1 H), 6.97 (d, J=1.7 H), 7.20 (dd, J=1.7, 7.9 Hz, 1 H), 7.31 (s, 1 H), 7.39–7.54 (m, 8 H), 8.17 (d, J=8.4 Hz, 2 H).

(Z)-4-{[8-(4-tert-Butylphenyl)-5,5-dimethyl-5,6-dihydronaphthalen-2-yl]-trimethylsilanylvinyl}benzyl Alcohol. (Compound 29)

Compound 29

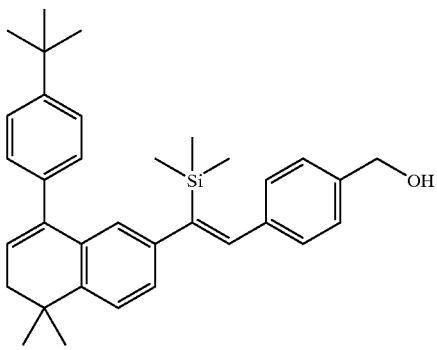

Following General Procedure A, 4-[(trimethylsilyl)ethynyl]benzyl tert-butyldiphenylsilyl ether and 6-bromo-4-(tert-butylphenyl)-1,1-dimethyl-1,2-dihydronaphthalene (which can be prepared by the procedure described in Klein, et al., U.S. Pat. No. 5,952,345) were coupled to give the title compound (Compound 29). PNMR (300 MHz, CDCl$_3$): δ0.0 (s, 9 H), 1.48 (s, 6 H), 1.51 (s, 9 H), 2.49 (d, J=4.8 Hz, 2 H), 4.82 (d, J=4.8 Hz, 2 H), 6.13 (t, J=4.8 Hz, 1 H), 7.00 (d, J=1.7 Hz, 1 H), 7.22 (dd, J=1.7, 7.9 Hz, 1 H), 7.30–7.50 (m, 8 H), 7.55 (d, J=8.8 Hz, H).

Ethyl (Z)-4-{[8-(4-tert-Butylphenyl)-5,5-dimethyl-5,6-dihydronaphthalene-2-yl]-trimethylsilanylvinyl}benzoate.(Compound 30)

(Compound 30)

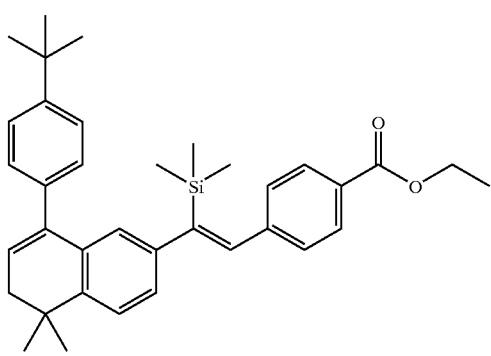

Following General Procedure B, (Z)-4-{[8-(4-tert-butylphenyl)-5,5-dimethyl-5,6-dihydronaphthalene-2-yl]trimethylsilanylvinyl}benzyl alcohol was oxidized to give the title compound (Compound 30). PNMR (300 MHz, CDCl$_3$): δ0.0 (s, 9 H), 1.49 (s, 15 H), 1.53 (t, J=7.1 Hz, 3 H), 2.50 (d, J=4.4 Hz, 2 H), 4.51 (q, J=7.1 Hz, 2 H), 6.13 (t, J=4.4 Hz, 1 H), 6.98 (d, J=2.2 Hz, 1 H), 7.20 (dd, J=2.2, 8.0 Hz, 1 H), 7.31 (s, 1 H), 7.40–7.54 (m, 7 H), 8.12 (d, J=8.4 Hz, 2 H).

(Z)-4-{[8-(4-tert-Butylphenyl)-5,5-dimethyl-5,6-dihydronaphthalene-2-yl]-trimethylsilanylvinyl}benzoic Acid.(Compound 31)

(Compound 31)

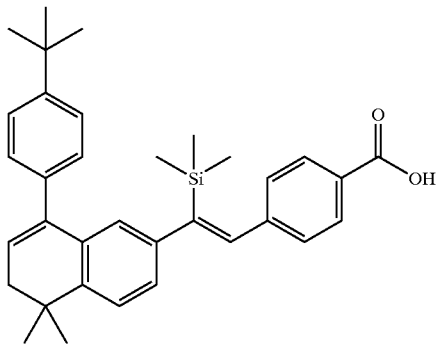

Following General Procedure C, ethyl (Z)-4-{[8-(4-tert-butylphenyl)-5,5-dimethyl-5,6-dihydronaphthalen-2-yl]trimethylsilanylvinyl}-benzoate was hydrolyzed to give the title compound (Compound 31). PNMR (300 MHz, CDCl$_3$): δ0.0 (s, 9 H), 1.49 (s, 15 H), 2.50 (d, J=4.8 Hz, 2 H), 6.13 (t, J=4.8 Hz, 1 H), 6.96 (d, J=2.2 Hz, 1 H), 7.20 (dd, J=2.2, 7.9 Hz, 1 H), 7.31 (s, 1 H), 7.44–7.54 (m, 7 H), 8.18 (d, J=8.4 Hz, 2 H).

(Z)-4-[2-(3,5-Di-tert-butylphenyl)-2-trimethylsilanylvinyl]benzyl Alcohol (Compound 32)

(Compound 32)

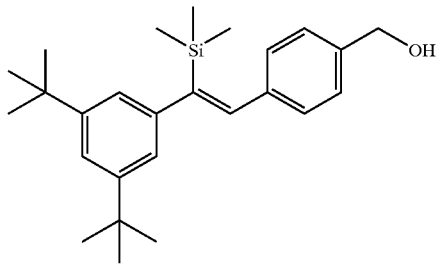

Following General Procedure A, 4-[(trimethylsilyl)ethynyl]benzyl tert-butyldiphenylsilyl ether and 1-bromo-3,5-Di-tert-butylbenzene (which can be prepared by the procedure described in Komen and Bickel Synth. Commun, 1996, 26, 1693–1698) were coupled to give the title compound (Compound 32). PNMR (300 MHz, CDCl$_3$) δ7.40 (s, 4H), 7.33 (s, 2H), 7.08 (s, 1H), 7.07(s, 1H), 4.78 (d, J=5.9 Hz, 1H), 1.41 (s, 18H), 0.00 (s, 9H).

Ethyl 4-[2-(3,5-Di-tert butylphenyl)-2-trimethylsilanylvinyl]benzoate.(Compound 33)

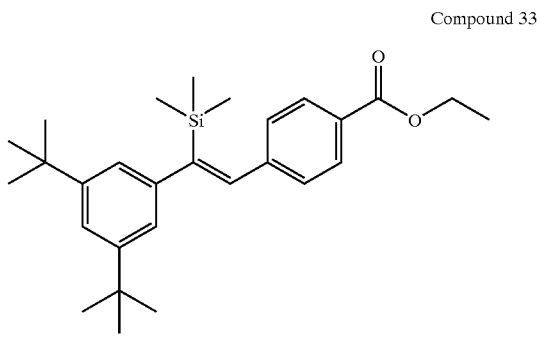

Compound 33

Following General Procedure B, (Z)-4-[2-(3,5-Di-tert-butylphenyl)-2-trimethylsilanylvinyl]benzyl alcohol was oxidized to give the title compound (Compound 33). PNMR (300MHz, CDCl$_3$) δ8.08 (d, J=8.4 Hz, 2H), 7.46 (d, J=8.5 Hz, 2H), 7.32 (m, 2H), 7.07 (s, 1H), 7.06 (s, 1H), 4.45 (q, J=7.2 Hz, 2H), 1.47 (t, J=7.2 Hz, 3H), 1.41 (s, 18H), 0.00 (s, 9H).

4-[2-(3,5-Di-tert-butylphenyl)-2-trimethylsilanylvinyl]benzoic Acid. (Compound 34)

prepared by the procedure described in Komen and Bickel Synth. Commun, 1996, 26, 1693–1698) were coupled to give the title compound (Compound 32). PNMR (300 MHz, CDCl$_3$) δ7.40 (s, 4H), 7.33 (s, 2H), 7.08 (s, 1H), 7.07(s, 1H), 4.78 (d, J=5.9 Hz, 1H), 1.41 (s, 18H), 0.00 (s, 9H).

Ethyl 4-[2-(3,5-Di-tert-butylphenyl)-2-trimethylsilanylvinyl]benzoate.(Compound 33)

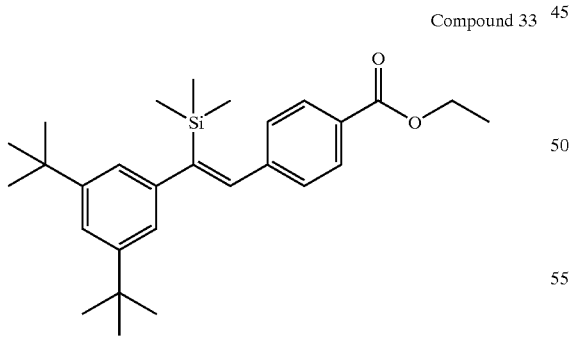

Compound 33

Following General Procedure B, (Z)-4-[2-(3,5-Di-tert-butylphenyl)-2-trimethylsilanylvinyl]benzyl alcohol was oxidized to give the title compound (Compound 33). PNMR (300MHz, CDCl$_3$) δ8.08 (d, J=8.4 Hz, 2H), 7.46 (d, J=8.5 Hz, 2H), 7.32 (m, 2H), 7.07 (s, 1H), 7.06 (s, 1H), 4.45 (q, J=7.2 Hz, 1.47 (t, J=7.2 Hz, 3H), 1.41 (s, 18H), 0.00 (s, 9H).

4-[2-(3,5-Di-tert-butylphenyl)-2-trimethylsilanylvinyl]benzoic Acid. (Compound 34)

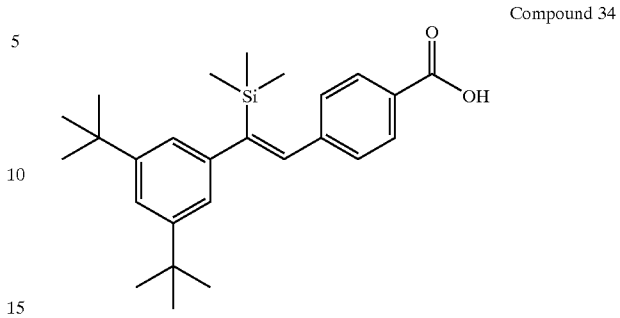

Compound 34

Following General Procedure C, ethyl 4-[2-(3,5-Di-tert-butylphenyl)-2-trimethylsilanylvinyl]-benzoate was hydrolyzed to give the title compound (Compound 34). PNMR (300 MHz, acetone-d$_6$) δ8.09 (d, J=8.2 Hz, 2H), 7.55 (d, J=7.9 Hz, 2H), 7.39 (m, 2H), 7.13 (s, 1H), 7.14 (s, 1H), 1.39 (s, 18H), 0.00 (s, 9H).

The examples set forth herein are meant to be illustrative only, and are not intended to limit the scope of the invention, which should be defined solely with reference to the claims that conclude this specification.

What is claimed is:

1. A compound selected from the group consisting of Formulas 1, 2, 3 and

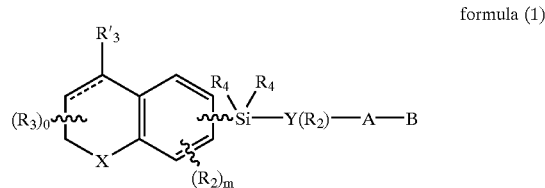

formula (1)

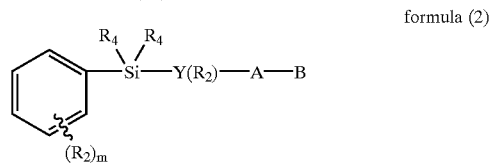

formula (2)

wherein the dashed line represents a bond or absence of a bond;

X is S, O, NR' where R' is H or alkyl of 1 to 6 carbons, or

X is (C(R$_1$)$_2$)$_n$ where R$_1$ is H or alkyl of 1 to 6 carbons, and n is an integer

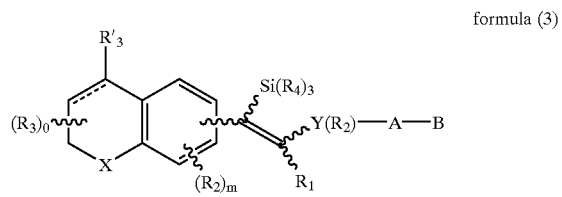

formula (3)

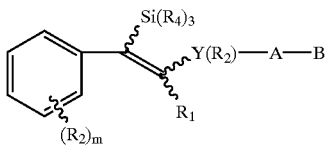

formula (4)

having the value of 0 or 1;

R$_2$ is hydrogen, lower alkyl of 1 to 6 carbons, F, Cl, Br, I, CF$_3$, fluoro substituted alkyl of 1 to 6 carbons, OH, SH, alkoxy of 1 to 12 carbons, or alkylthio of 1 to 12 carbons, benzyloxy or C$_1$–C$_{12}$ alkylbenzyloxy;

R$_3$ is hydrogen, lower alkyl of 1 to 6 carbons or F;

m is an integer having the value of 0–3;

o is an integer having the value of 0–4 when the dashed line represents absence of a bond, and 0–3 when the dashed line represents a bond;

R$_3'$ is hydrogen, lower alkyl of 1 to 6 carbons, F or (R$_{15}$)$_r$-phenyl, (R$_{15}$)$_r$-naphthyl, or (R$_{15}$)$_r$-heteroaryl where the heteroaryl group has 1 to 3 heteroatoms selected from the group consisting of O, S and N, r is an integer having the values of 0–5;

R$_4$ is alkyl of 1 to 8 carbons or phenyl;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two R$_2$ groups;

R$_{15}$ is independently H, F, Cl, Br, I, NO$_2$, N(R$_8$)$_2$, NH(R$_8$), COR$_8$, NR$_8$CON(R$_8$)$_2$, OH, OCOR$_8$, OR$_8$, CN, an alkyl group having 1 to 10 carbons, fluoro substituted alkyl group having 1 to 10 carbons, an alkenyl group having 1 to 10 carbons and 1 to 3 double bonds, alkynyl group having 1 to 10 carbons and 1 to 3 triple bonds, or a trialkylsilyl or trialkylsilyloxy group where the alkyl groups independently have 1 to 6 carbons;

A is (CH$_2$)$_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH, NO$_2$, P(O)(OH)$_2$, P(O)(OH)OR$_8$, P(O)(OR$_8$)$_2$, SO$_2$OH, SO$_2$(OR$_8$), COOR$_8$, CONR$_9$R$_{10}$, —CH$_2$OH, CH$_2$OR$_{11}$, CH$_2$OCOR$_{11}$, CHO, CH(OR$_{12}$)$_2$, CHOR$_{13}$O, —COR$_7$, CR$_7$(OR$_{12}$)$_2$, CR$_7$OR$_{13}$O, or tri-lower alklsilyl, where R$_7$ is an alkyl, cycloalkyl or alkenyl group containing 1 to 5 carbons, R$_8$ is an alkyl group of 1 to 10 carbons or trimethylsilylalkyl where the alkyl group has 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5–10 carbons, or phenyl or lower alkylphenyl, R$_{11}$ is lower alkyl, phenyl or lower alkylphenyl, R$_{12}$ is lower alkyl, and R$_{13}$ is divalent alkyl radical of 2–5 carbons, or a pharmaceutically acceptable salt of said compound.

2. A compound in accordance with claim 1 where X is (C(R$_1$)$_2$)$_n$ and n is 1.

3. A compound in accordance with claim 1 where X is S.

4. A compound in accordance with claim 1 where X is O.

5. A compound in accordance with claim 1 where X is NR=.

6. A compound in accordance with claim 1 where Y is phenyl.

7. A compound in accordance with claim 1 where Y is thienyl.

8. A compound in accordance with claim 1 having a structure selected from formulas (1) and (2).

9. A compound in accordance with claim 8 having a structure of formula (1) where the dashed line represents absence of a bond.

10. A compound in accordance with claim 8 having a structure of formula (1) where the dashed line represents a bond.

11. A compound in accordance with claim 1 having a structure selected from formulas (3) and (4).

12. A compound in accordance with claim 11 having a structure of formula (3) where the dashed line represents absence of a bond.

13. A compound in accordance with claim 11 having a structure of formula (3) where the dashed line represents a bond.

14. A compound of the formula

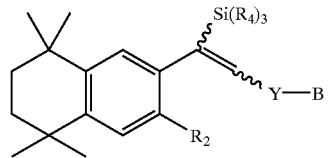

where R$_2$ is H or methyl, R$_4$ is lower alkyl of 1 to 8 carbons, Y is phenyl or thienyl and B is CH$_2$OH, or COOR$_8$ where R$_8$ is H or ethyl.

15. A compound in accordance with claim 14 where R$_4$ is methyl.

16. A compound in accordance with claim 15 where Y is phenyl.

17. A compound in accordance with claim 16 where R$_2$ is H.

18. A compound in accordance with claim 17 where B is CH$_2$OH.

19. A compound in accordance with claim 17 where B is COOR$_8$.

20. A compound in accordance with claim 16 where R$_2$ is CH$_3$.

21. A compound in accordance with claim 20 where B is CH$_2$OH.

22. A compound in accordance with claim 20 where B is COOR$_8$.

23. A compound in accordance with claim 15 where Y is thienyl.

24. A compound in accordance with claim 23 where R$_2$ is H.

25. A compound in accordance with claim 24 where B is CH$_2$OH.

26. A compound in accordance with claim 24 where B is COOR$_8$.

27. A compound of the formula

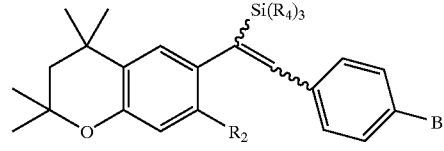

where R$_2$ is H or methyl, R$_4$ is lower alkyl of 1 to 8 carbons and B is CH$_2$OH, or COOR$_8$ where R$_8$ is H or ethyl.

28. A compound in accordance with claim 27 where R$_2$ is H.

29. A compound in accordance with claim 28 where B is CH$_2$OH.

30. A compound in accordance with claim 29 where B is COOR$_8$.

31. A compound of the formula

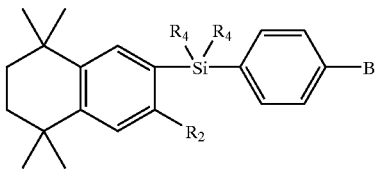

wherein R$_2$ is H or lower alkyl, R$_4$ is lower alkyl of 1 to 8 carbons and B is CH$_2$OH or COOR$_8$ where R$_8$ is H or ethyl.

32. A compound in accordance with claim 31 where R$_2$ is H and R$_4$ is ethyl.

33. A compound in accordance with claim 32 where B is CH$_2$OH.

34. A compound in accordance with claim 33 where B is COOR$_8$.

\* \* \* \* \*

UNITED STATES PATENT AND TRADEMARK OFFICE
CERTIFICATE OF CORRECTION

PATENT NO. : 6,452,032 B1
DATED : September 17, 2002
INVENTOR(S) : Beard et al.

It is certified that error appears in the above-identified patent and that said Letters Patent is hereby corrected as shown below:

Column 5,
Line 43, delete "Remnington's" and insert in place thereof -- Remington's --

Column 13,
Line 67, delete "TBF" and insert in place thereof -- THF --

Column 14,
Line 46, delete "brorninated" and insert in place thereof -- brominated --

Column 18,
Line 10, delete "scarification" and insert in place thereof -- saponifaction --

Column 26,
Line 26, delete "tetrdronaphthalen" and insert in place thereof -- tetradronaphthalen --

Column 28,
Line 18, after "benzyl" delete "030"

Column 29,
Line 6, delete "(d, J=1.7H)" and insert in place thereof -- (d, J=1.7 Hz, 1H) --

Signed and Sealed this

Twenty-eighth Day of January, 2003

JAMES E. ROGAN
*Director of the United States Patent and Trademark Office*